US008656918B1

(12) United States Patent
Alley et al.

(10) Patent No.: US 8,656,918 B1
(45) Date of Patent: Feb. 25, 2014

(54) METHOD, SYSTEM, AND TOOL FOR AFFIXING COMPRESSION STABILIZED PROSTHETIC SOCKET INTERFACE

(75) Inventors: Randall D. Alley, Thousand Oaks, CA (US); T. Walley Williams, III, Belmont, MA (US)

(73) Assignee: Randall D. Alley, Thousand Oaks, CA (US)

(*) Notice: Subject to any disclaimer, the term of this patent is extended or adjusted under 35 U.S.C. 154(b) by 74 days.

(21) Appl. No.: 13/334,952

(22) Filed: Dec. 22, 2011

Related U.S. Application Data

(63) Continuation-in-part of application No. 12/945,876, filed on Nov. 14, 2010, now Pat. No. 8,323,353, which is a continuation-in-part of application No. 12/792,728, filed on Jun. 2, 2010, now abandoned, which is a continuation-in-part of application No. 12/380,861, filed on Mar. 4, 2009, now abandoned.

(60) Provisional application No. 61/068,263, filed on Mar. 4, 2008.

(51) Int. Cl.
*A61G 15/00* (2006.01)
(52) U.S. Cl.
USPC .......................................... 128/845
(58) Field of Classification Search
USPC ......... 128/845, 846, 869, 870, 871, 878, 882;
602/5, 17, 19, 20, 23, 26, 27, 32,
602/60–63; 606/53–54; 623/909
See application file for complete search history.

(56) References Cited

U.S. PATENT DOCUMENTS

| 570,085 | A | * | 10/1896 | Clausson .......................... 602/5 |
| 1,272,179 | A | | 7/1918 | Anderson |
| 2,506,464 | A | | 5/1950 | Millheisler |
| 3,111,683 | A | | 11/1963 | Bach |
| 3,299,888 | A | * | 1/1967 | Muckinhaupt .................. 602/23 |

(Continued)

FOREIGN PATENT DOCUMENTS

| ES | 2157778 B1 | 8/2001 |
| WO | 9503760 A1 | 2/1995 |

OTHER PUBLICATIONS

Pre-Brief Appeal Conference Decision dated Apr. 11, 2012, U.S. Appl. No. 12/945,876.
Declaration of Randall D. Alley, executed Jun. 29, 2012.

(Continued)

*Primary Examiner* — Patricia Bianco
*Assistant Examiner* — Raymond E Harris
(74) *Attorney, Agent, or Firm* — Lubka & White LLP; Bruce Lathrop

(57) ABSTRACT

A method, system, and tool for fitting a compression stabilized prosthetic socket for a patient having an amputated limb and a remaining portion that includes a first socket portion for contacting a patient's remaining portion of a limb, and a second socket portion for attachment of a prosthetic device. The first socket portion has compression portions having a radius for compressing portions of the patient's remaining portion of a limb, and relief portions receiving any portions of the patient's remaining limb which bulge upon the compression applied by the compression portions. The relief portions may be formed as openings or as enlarged radius portions. The fitting method, system, and tool can include use of a mechanism to compress bar surfaces against the limb in areas selected to receive compression portions in order to prepare an image for creating the first socket portion.

35 Claims, 18 Drawing Sheets

(56) References Cited

U.S. PATENT DOCUMENTS

| | | | |
|---|---|---|---|
| 3,520,002 A | | 7/1970 | Wellington |
| 3,829,079 A | * | 8/1974 | Fox ................................. 5/621 |
| 4,024,860 A | * | 5/1977 | Chelnokov et al. ............. 602/32 |
| 4,128,903 A | | 12/1978 | Marsh |
| 4,459,709 A | | 7/1984 | Leal |
| 4,921,502 A | * | 5/1990 | Shamp ............................ 623/33 |
| 5,003,969 A | * | 4/1991 | Azer et al. ...................... 606/54 |
| 5,101,815 A | * | 4/1992 | Langdon-Orr et al. ......... 602/12 |
| 1,893,853 A | | 1/1993 | Tullis |
| 5,288,286 A | | 2/1994 | Davis |
| 5,360,392 A | * | 11/1994 | McCoy .............................. 602/6 |
| 5,390,383 A | * | 2/1995 | Carn ................................. 5/624 |
| 5,405,405 A | | 4/1995 | Love |
| 5,458,599 A | * | 10/1995 | Adobbati ......................... 606/56 |
| 5,480,455 A | | 1/1996 | Norvell |
| 5,484,393 A | * | 1/1996 | McCoy .............................. 602/6 |
| 5,503,543 A | * | 4/1996 | Laghi ................................ 425/2 |
| 5,575,027 A | * | 11/1996 | Mueller ............................ 5/621 |
| 5,624,387 A | * | 4/1997 | McGuinness ................... 602/18 |
| 5,718,925 A | * | 2/1998 | Kristinsson et al. .............. 425/2 |
| 5,724,714 A | | 3/1998 | Love |
| 5,972,036 A | * | 10/1999 | Kristinsson et al. ............ 623/33 |
| 6,077,300 A | | 6/2000 | Sabolich |
| 6,362,387 B1 | | 3/2002 | Carlson |
| 6,712,780 B2 | * | 3/2004 | Darcey .............................. 602/8 |
| 6,991,657 B1 | | 1/2006 | Price, Jr. |
| 7,097,799 B1 | * | 8/2006 | Burton .......................... 264/223 |
| 7,377,944 B2 | | 5/2008 | Janusson |
| 8,323,353 B1 | | 12/2012 | Alley |
| 2002/0002405 A1 | * | 1/2002 | Janusson et al. ................ 623/36 |
| 2004/0049141 A1 | * | 3/2004 | Slautterback et al. .......... 602/21 |
| 2004/0158332 A1 | | 8/2004 | Carstens |
| 2007/0255424 A1 | | 11/2007 | Leydet |
| 2010/0274364 A1 | | 10/2010 | Pacanowsky |

OTHER PUBLICATIONS

"RCR Transtibial Socket", web page from www.coyotedesign.com, printed Dec. 11, 2009 (1 pg.).
Alley, U.S. Appl. No. 12/380,861, filed Mar. 4, 2009.
Office Action dated Feb. 2, 2010, U.S. Appl. No. 12/380,861.
Alley, U.S. Appl. No. 61/068,263, filed Mar. 4, 2008.
Alley, U.S. Appl. No. 12/792,728, filed Jun. 2, 2010.
"Biodesigns Inc Maximizing Human Performance", advertisement, inMotion Magazine, Apr. 2008 (1 page).
Randall Alley, "New Interface Design Benefits the High Performance Individual", article, Challenge Magazine, Jun. 2008 (1 page).
Alley, U.S. Appl. No. 12/945,876, filed Nov. 14, 2010.
Office Action dated Jan. 4, 2012, U.S. Appl. No. 12/945,876.
Notice of Allowance and Fee(s) Due, dated Jul. 30, 2012, U.S. Appl. No. 12/945,876.
Declaration of Randall D. Alley of Aug. 2013, executed Aug. 14, 2013.
Office Action mailed Mar. 10, 2011, U.S. Appl. No. 12/945,876.
Final Office Action mailed Jun. 23, 2011, U.S. Appl. No. 12/945,876.
Alley, U.S. Appl. No. 61/720,934, filed Oct. 31, 2012.
Alley, U.S. Appl. No. 61/732,493, filed Dec. 3, 2012.
Alley, U.S. Appl. No. 13/797,957, filed Mar. 12, 2013.
Randall D Alley, "Prosthetic sockets stabilized by alternating areas of tissue compression and release," Journal of Rehabilitation Research & Development, vol. 48 No. 6, 2011, pp. 679-696.
Alley, U.S. Appl. No. 13/663,282, filed Oct. 29, 2012.
Office Action mailed Jan. 6, 2014, U.S. Appl. No. 13/663,282.

* cited by examiner

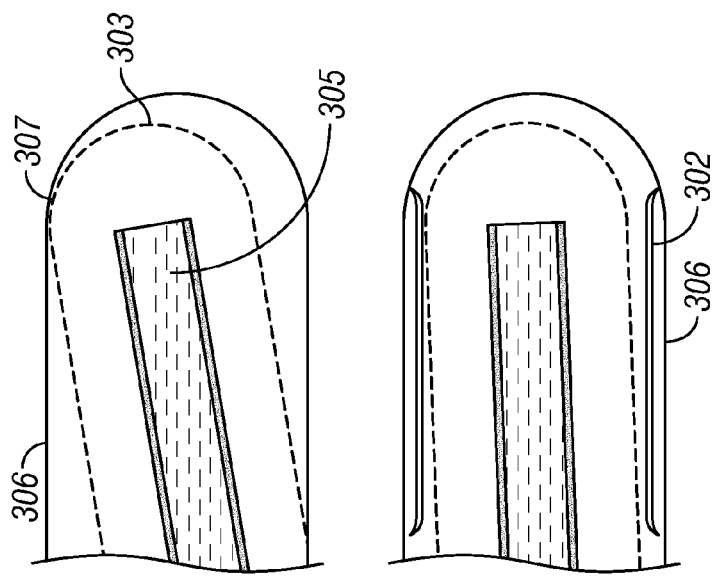
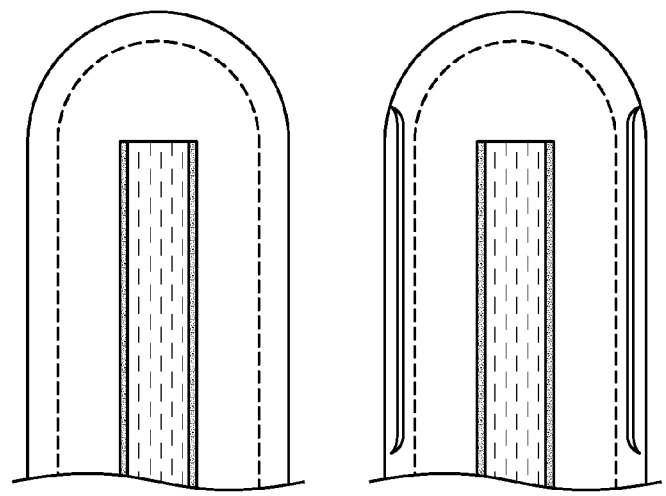
FIG. 16
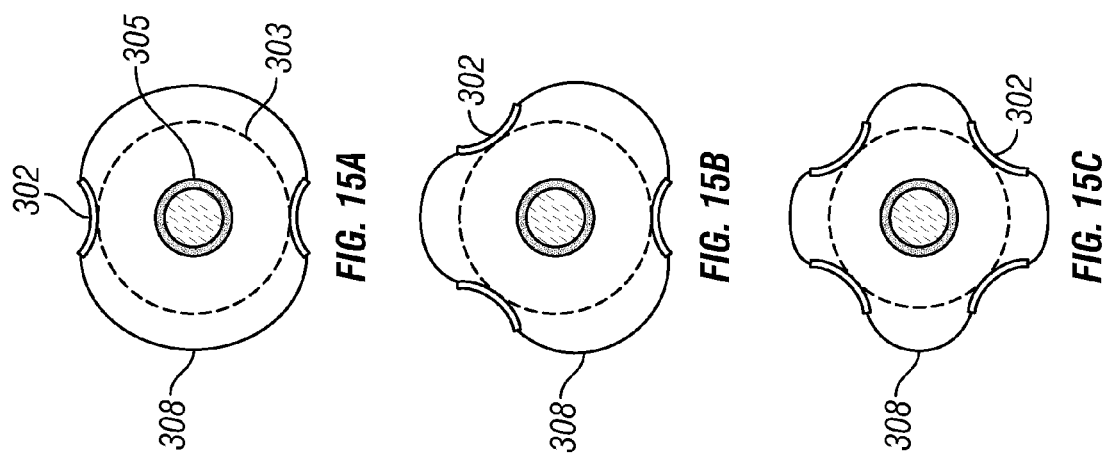
FIG. 15A
FIG. 15B
FIG. 15C

METHOD, SYSTEM, AND TOOL FOR AFFIXING COMPRESSION STABILIZED PROSTHETIC SOCKET INTERFACE

CROSS REFERENCE TO RELATED APPLICATION(S)

This application is a continuation-in-part of, and claims the benefit of priority from U.S. patent application Ser. No. 12/945,876, filed Nov. 14, 2010, now U.S. Pat. No. 8,323,353, which in turn is a continuation-in-part of, and claims the benefit of priority from U.S. patent application Ser. No. 12/792,728, filed Jun. 2, 2010, now abandoned, which in turn is a continuation-in-part of, and claims the benefit of priority from U.S. patent application Ser. No. 12/380,861, filed Mar. 4, 2009, now abandoned, which in turn claims benefit of U.S. Provisional Patent Application No. 61/068,263, filed Mar. 4, 2008, all four of such applications are incorporated by reference herein.

FIELD OF THE INVENTION

The present invention relates to the prosthetic limbs worn by upper or lower limb amputees and in particular, to the portion of a limb prosthesis that is in direct contact with the user's skin.

DEFINITIONS OF TERMS

Socket—is that part of a prosthesis in direct contact with the user's skin. The word Socket usually implies a traditional socket that is essentially circular in cross section. A traditional prosthesis consists of an inner socket to interface with the user's skin and an outer socket over it that continues to incorporate the mechanisms that comprise the next distal structure which may be a joint or a device to function as a foot or gripping device. The inner and outer sockets may be separate structures or may be unitary consisting of a single unit.

Interface—is often used as a synonym for socket, but is more often reserved for socket-like structures that have openings in the outer socket and occasionally in both the outer and inner sockets.

Cast—is a thin layer of wet plaster impregnated gauze wrapped around a residual limb and the surrounding body parts and then permitted to harden to reproduce the shape of the limb. While the plaster is hardening, pressure from the hands of the plaster technician often modifies the shape to accommodate the underlying boney anatomy.

Positive Model—is the plaster model that results from filling a cast with plaster or similar material. Modifications by adding and subtracting plaster are made to this model before its outer surface is used to define the shape of the user's socket or interface.

Check Socket—is a temporary socket made over the model and used to test whether the modifications have had the desired effect on the fit of the resulting socket.

Channel—is used here to describe a longitudinal area where the wall of a socket is depressed inward as close to the underlying skeletal structures as is comfortable.

Relief Area—is the region in a socket system between two channels or around or near a compressed area which provides a place for the displaced tissue to migrate.

Lost Motion—is the motion of the skeletal structures with respect to the prosthetic interface when force is applied between the two as would occur as an amputee tries to move the prosthesis as a whole. In a traditional socket, lost motion occurs when the bone moves toward the socket wall a substantial distance before imparting force to the wall.

Compression Bar—is a long flat bar typically a little shorter than the shaft of the remaining long bone(s). The width of the bar is usually about ten percent of the circumference of the remaining limb.

Optimal Tissue Compression—is compression of the tissue against the socket wall such that lost motion is minimized without causing discomfort to the user.

High-fidelity Interface or device—is the name given to the socket or interface that utilizes compression stabilization as the basis for its function and physical structure.

BACKGROUND OF THE INVENTION

Historically the prosthetic user interface has been a cylindrical socket that merely surrounds the remaining limb part with some contouring of the proximal brim so that it will accommodate the shape of the next proximal joint or body part. Typically, this socket is made by taking a plaster cast over the limb and filling it with plaster to form a positive model of the limb. Minor changes are made to this shape to relieve boney prominences. When this model is used to create a socket by laminating or thermoforming a layer of plastic there over, the resulting socket mainly encapsulates the limb part. Conventionally, no modification of the traditional model is done. This opportunity to specifically enhance the resulting structure's ability to impart desired motion to the complete prosthesis, and to prevent undesired motion from occurring, has been overlooked, even though these are the most important functions of the interface. The traditional encapsulating or closed volume socket merely contains the soft tissue but does little or nothing to prevent lost motion between the socket and the underlying skeletal structure.

Some improvements have been made in the traditional interface. In particular, many technicians replace the fully encapsulating outer socket with a frame having one or more openings. This change is accompanied by making the inner socket of a flexible material. The resulting frame-style design usually is more comfortable. New materials such as carbon fiber composites add rigidity where needed especially in open frame designs. New flexible materials allow the socket wall to flex in other areas for comfort. Even when these newer flexible materials are used, the soft liner still fully encapsulates the remaining limb as traditionally done, and thus provides a compressive or elastic force to all of the limb's soft tissue.

Conventional laminations over a plaster model work best when the surfaces of the model are convex facing outward, following the general contours of the outside surface of the limb.

SUMMARY OF THE INVENTION

In a preferred embodiment of the invention, a mold (negative model) is made by making a cast of a remaining limb on which a prosthesis will be used. From the mold/cast, a positive model is made of the remaining limb. There are deep channels formed in the positive model, which are a cause of excessive thickness in these areas when conventional lamination procedures are used. Where the areas between the channels are to be left open, however, the model may be brought almost flush with the edges of the compressed areas. This alteration permits a much stronger lamination. Another technique to strengthen the resulting struts is to corrugate the compression channel area to create a resistance to flex upon lamination.

When taking a cast of the area above the knee, prosthetists are often assisted by using jigs especially to establish the shape of the socket brim area for transfemoral sockets. In the new socket technology of this invention, one may also use a jig to assist in achieving an optimal cast of the area above the knee.

Preventing Lost Motion

In one embodiment, a basis of this invention stems from a simple observation using a procedure such as described below. A person holds his/her arm in a fixed position so that an experimenter cannot easily move the arm side to side. The experimenter then pushes with a finger on the fleshy area over the long bone of the upper arm. Typically, the finger will push into the soft tissue a centimeter or more before it compresses the tissue against the bone and no further motion is possible without the subject moving. During compression, tissue moves aside away from the area of compression. From the inventor's knowledge, no prior designs have specifically allowed for the displacement of tissue as a requirement for achieving stability even if local compressed areas exist. For a long bone to be fully stabilized with respect to the prosthetic interface, compression must be applied in a specific way. Typically, three or four channels are created in the socket along the entire length of the bone except at the very ends. Accordingly, the channels extend proximate to ends of the bone, e.g. at least eighty and more preferably at least ninety percent of the existing longest bone in the existing limb. The inner surfaces of these channels compress the tissue against the long bone until little further motion is possible. For this compression to be effective, there must be a longitudinal relief area between each pair of channels. The channels and the relief areas are two key elements of a preferred embodiment of the invention and both must be present for optimal performance. In a more preferred embodiment, a third key element is that at least three channels are needed to impart full stability.

Creating the Compression Stabilized Socket Interface

The traditional prosthetic socket is created by taking a cast, making a positive model, and modifying the model to create a form for shaping a final socket interface. An important element of a preferred embodiment of this invention is the use of the traditional sequence in a new way. Three to four compression bars are made prior to taking the cast. These are tested by spacing them appropriately around the remaining limb and pushing in. Care is given to both the physical and anatomical structures of the limb in determining proper placement. In the case of the upper limb, specifically the humeral level in which positional precision and lifting capacity take precedent, the locations of these compression bars are biased toward stabilization in flexion and abduction, the two most common functional motions utilized, resulting in narrower relief windows in the anterior and lateral areas of the socket. The length, width, and curvature of the bars are adjusted until they lock the underlying bone in place when equal pressure is applied to the bars. The individual bars are checked to see if they rock end-to-end when pressure is shifted in which case a change in shape is indicated. Before taking the cast, the prosthetist must decide how to arrange the bars around the limb so that forces are optimally transmitted when the resulting interface is used. The underlying location of nerves and other structures will determine the exact angular orientation of the bars and may determine the optimum number of bars to use.

The cast is taken by applying a loose wrap of wet elastic casting plaster. The bars are then placed in the pre-planned positions, pressed into the elastic wrap and soft tissue by hand or with a casting jig with sufficient force to impart substantial compression on the limb and held in place while the plaster sets. It is important for the wrap to be able to stretch so that the displaced tissue has somewhere to go. Even in the best of circumstances, the plaster will prevent the bars from achieving optimal penetration. This is corrected during the cast rectification stage. Before, during or after the channels in the plaster and the bulges in between are sufficiently set, the proximal parts of the cast are taken in the usual manner. However, some areas in this secondary area of the wrap may also need to be compressed by the fingers of the cast taker to create additional areas of pre-compression.

For taking a femoral level cast, the distances and forces needed are greater and a bar-location jig is of great help. This jig is an integral part of the invention for femoral casting and femoral interface sockets and could also be used if desired for humeral casting. The jig consists of two or more stiff "d"- or "c"-shaped rings with the flattened surface of the d-rings or the open surface of the c-rings positioned to the medial or inside area next to the midline of the body or the opposite leg if present. These rings are large enough to allow some space inside the rings when they are placed around the limb. Each ring can accept a single screw attachment or plurality of screw attachments. Each attachment can be oriented azimuthally around the ring and then locked in place. Each attachment has a screw or screws aimed at the center of the ring capable of applying force to one of the channel-forming bars. In addition, the attachments are open on one of the sides that face parallel to the limb in the d-ring design. This opening permits the prosthetist to remove a single pair of attachments and the underlying bar after the preliminary setup described below. The c-ring design inherently already has this opening. Small snap-in pockets along the outside of each bar and the fact that the screw ends are spherical prevent slipping once the bars are in place. In the ideal embodiment, the pockets have a restriction at the opening that makes the attachment of the screw ends act like pop beads to hold the screw end to the bar. In a typical cast taking at the femoral level, two rings are used and each has four attachments oriented approximately ninety degrees apart. In the design utilizing two screws for each compression bar, the attachment screws are placed in pockets on the bars about twenty percent of the length of the bar in from the end. Before the cast is taken, the prosthetist experiments and selects the best length and width for each bar and the optimal location. To speed application during the actual cast taking, all positions are marked with the anticipated extra circumference of the added plaster wrap accounted for.

An alternative jig in accordance with the invention has a support member to support and position channel-forming bars, or paddles, so that the paddle surfaces can be maneuvered to press inwardly against target compression areas for a selectable distance and permit displacement of tissue to uncompressed areas. In a particular embodiment, the paddles are removable, so the user can choose the number, shape, and size of paddles desired. Four paddles may be advantages in particular applications.

The operation of maneuvering, for example, can be accomplished with a projection member connected to and actuated by an attachment mechanism, which is attachable to the support member. The attachment mechanism can advantageously be movable along the support member and locked into a desired location. A particular attachment mechanism can be operable to press the projection member inwardly against the body part and to lock the projection member in place when it has reached the distance required for the desired compression.

The support member, for example, can be attachable at particular locations to a stand, which is suitable to support a patient. The support member can then be moved up or down along the stand to adjust the jig to the size of the patient and the desired imaging area. To further support the patient, a particular example includes a handle on the upper end of the stand. In an advantageous example, the support member can pivot on the stand, so a user can further maneuver the support member and the attached paddles into a desired position for imaging. The support member can be removed from the stand, for example, to allow different sized support members to be attached and used with the stand.

After the cast has been filled to create a positive model, the plaster technician will usually need to deepen the channels before pulling a thermoformed check socket out of transparent plastic. If a solid-bodied check socket will be utilized, then additional plaster must be added over the relief areas of the positive model to allow sufficient displacement of soft tissue into the check socket's relief areas. Usually several check sockets will be needed. As each is applied to the user, the fit and stability of the check socket is evaluated. The color of the tissue will tell the experienced practitioner where too much compression is being applied and where there is too little. In addition, substantial forces should be applied in all directions to ensure that the stabilization is optimal. Since the compression stabilized interface design requires that the areas between channels be left free or sufficiently relieved for tissue movement, there is good reason for leaving these areas fully open in the check socket unless an encapsulating or solid-body interface is desired. The user can then more readily perspire and dissipate excess body heat. With three or more long openings in the socket wall, a traditional cloth laminate is usually replaced by a stiff, strong carbon fiber reinforced laminate in the form of a frame.

Usually a temporary assembly of the distal prosthetic components is added to the final check socket and tested before the shape of the check socket is approved for creating the definitive prosthesis. For approval, the interface must transmit force and motion to the prosthesis in every direction that the user will require with minimal lost motion between the interface and the rest of the prosthesis.

In a presently preferred embodiment of the invention, there is a limb interface device. The limb interface device has either an encapsulating design with adequate soft tissue reliefs or an open cage or strut-type configuration of rigid, semi-rigid, or dynamically adjustable struts appropriately contoured to a patient's residual limb. The open cage or strut-type configuration contains windows through which soft tissue can flow out of the interface confines.

The limb interface device may have any of various prosthetic components attached to it to provide an upper or lower extremity prosthesis extending from the distal end of the interface device. The regions of compression in both the encapsulating and strut-type embodiments are configured and aligned in such a way as to transfer skeletal movement as efficiently as possible such that interface response to volitional movement and interface stability are maximized. Optionally, stabilizers or other devices may be attached to a proximal end of the limb interface device.

In the open cage or strut-type configuration, the strut edges can be configured such that they are either flexible enough or shaped appropriately to mitigate edge pressure and hence soft tissue stress, or a material can be fitted to the struts such that it extends just beyond the border of the rigid or semi-rigid edge and provides a more gradual transition of pressure at this location.

In another preferred embodiment, the interface device may have the ability to alter the stiffness of the strut assembly itself on demand or automatically in response to applied loads such that edge pressure or overall strut compression is varied appropriately to prevent skin or underlying soft tissue damage. Finally, an inner, highly flexible membrane may be utilized that encapsulates the entirety of the limb and is placed between the strut assembly and the limb yet still allows sufficient soft tissue flow beyond the confines of the strut assembly such that edge pressure on the soft tissue and redundant intrinsic skeletal motion are minimized.

Although embodiments of the present interface assembly finds particular application with prosthetic limbs, it is also to be appreciated that the interface assembly may be used in other applications such as orthotics or other interface applications involving the human body.

Still other objects, advantages and constructions of the present invention, among various considered improvements and modifications, will become apparent from the detailed description provided hereinafter. It should be understood that the detailed description and specific examples, while indicating a presently preferred embodiment of the invention, are intended for purposes of illustration only and are not intended to limit the scope of the invention.

In some parts of the orthotic and prosthetic industry, cast taking has been replaced by laser scanning of the residual limb and the creation of a virtual solid model. It is anticipated that simple algorithms can be created to permit insertion of channels and bulges in a virtual model such that the area inside the virtual wall of any cross section of the residual limb would remain the same. Such an algorithm automatically creates appropriate bulges when the technician moves a portion of the wall toward the skeletal structures in the virtual model. Principles of the embodiments of the invention are not changed when the model for creating the definitive interface structure is based on a plaster cast or on a virtual model produced with software.

In a preferred embodiment, there is a prosthetic socket which prevents lost motion between an amputee's remaining limb and the prosthesis by selectively compressing tissue against the bone in some areas while providing relief in other areas so that displaced tissue is accommodated when forces are applied between the bone and the interface. Additional embodiments of the invention include methods for creating the new socket design.

It is an object of various embodiments of the present invention to provide a prosthetic interface within which the individual's upper or lower extremity residual limb part is captured with greater stability than in known prior art.

It is a further object of various embodiments of the invention to provide a mechanism to selectively compress the soft tissue between the residual limb's skeletal structure and socket structures to minimize lost motion when the skeletal structures of the residual limb move with respect to the socket and attached prosthesis.

It is a further object of various embodiments of the present invention to provide a plurality of areas of compression parallel to the long axis of the major bone or bones of the residual anatomy.

It is a further object of various embodiments of the present invention to provide open or low-compression relief areas between said areas of compression so that said compression is not impeded by the inability of the underlying tissue to flow or migrate sideways.

It is a further object of various embodiments of the present invention to provide a method for taking a cast of the residual limb that results in an approximation of the desired final shape of the socket interface.

It is a further object of various embodiments of the present invention to create areas of compression in a plaster cast parallel to the long axis of the residual limb during the process of cast taking with bulges in between that will define areas of relief in the complete prosthetic interface.

It is a further object of various embodiments of the present invention to provide check sockets where areas of relief are created by leaving the socket wall completely open or are large enough in the encapsulating version to allow for sufficient soft tissue displacement.

It is a further object of various embodiments of the present invention to provide definitive prosthetic interfaces where areas of compression, both with respect to the underlying bone as well as with respect to the area of compression just proximal to the bulging soft tissue, to stabilize the longitudinal motion of the prosthesis with respect to the skeletal anatomy thus aiding in suspension and weight bearing.

It is a further object of various embodiments of the present invention to provide definitive prosthetic sockets where a soft liner covers the limb but is stabilized by a frame there over with the frame performing the functions of a traditional outer socket. (If such a liner is used, the model over which it is formed must have bulges between the compression channels large enough to create a liner with little or no tissue compression in the areas between the areas of compression.)

It is a further object of various embodiments of the invention to provide areas into or through which a significant amount of soft tissue of the said limb can flow freely, without restriction or with minimal restriction so as to permit sufficient soft tissue flow away from areas of compression along the shaft of the bone or bones in the aforementioned areas of high compression.

It is a further object of various embodiments of the present invention to take advantage of the anatomical response such that tissue can be compressed against bone just so far before further motion is impeded if there is room for the displaced tissue to move out of the way.

It is a further object of various embodiments of the present invention to create prosthetic sockets with longitudinal grooves alternated with areas sufficiently open that the displaced tissue suffers no compression.

It is a further object of various embodiments of the present invention to create sockets that have three or more compression channels so that lost motion is prevented in all directions.

It is a further object of various embodiments of the present invention to shape the interior surfaces of the grooves such that when the prosthesis is loaded the local pressure along the length of the bone is equal without excessive pressure at the ends.

It is a further object of various embodiments of the present invention to provide means for creating a prosthetic interface by applying a plurality of bars or a loose plaster wrap during the cast taking procedure.

It is a further object of various embodiments of the present invention to provide a jig for holding the bars in position during cast taking.

It is a further object of various embodiments of the present invention to provide a jig having two or more rings larger in diameter than the limb. Each ring has a single or plurality of snap-in-place screw holder(s) with adjustment screws oriented so the axis of the screw passes through the center of the ring.

It is a further object of various embodiments of the present invention to provide screw holders that are applied to the ring by moving parallel to the axis of the ring. This feature permits a bar screw holder or a bar and two screw holders to be removed from a pair of rings as a unit.

It is a further object of various embodiments of the present invention to provide adjustment screws with spherical ends.

It is a further object of various embodiments of the present invention to provide a snap-in socket or plurality of snap-in sockets along the center line of the outside of each bar which accept the spheres on the adjustment screws.

It is a further object of various embodiments of the present invention to provide bars with center sections that telescope so bar length can be adjusted as well as to offer different length bars to be snapped in place depending on the application.

It is a further object of various embodiments of the present invention to provide a jig having a support member attached to a stand where the support member is maneuverable to press paddles against target compression areas selectable distances and permit displacement of tissue to uncompressed areas.

It is a further object of various embodiment of the present invention to provide a jig with a stand that can support a patient and where the stand can be adjustable to accommodate patients of different sizes.

It is a further object of the various embodiment of the present invention to provide a jig with different sized support members for different sized patients.

It is a further object of various embodiments of the present invention to provide a jig having projection members for pressing paddles, where the projection members can be moved along a support member to position the projection members to press against particular target compression areas.

It is a further object of various embodiments of the present invention to provide a jig that locks paddle surfaces in place once the paddle surfaces are maneuvered to press on target compression areas a selectable inward distance.

BRIEF DESCRIPTION OF THE DRAWINGS

FIG. 15A-C is a drawing showing compression bars pressing against two, three, or four target areas on a limb to a maximum compression point in order to capture the motion of the underlying bone, while allowing displacement of tissue into noncompressed areas.

FIG. 16 is a drawing illustrating motion capture of the underlying bone by compression bars in comparison to the broader motion that is experienced without compression bars.

DESCRIPTION OF THE PREFERRED EMBODIMENT(S)

Figure 1:
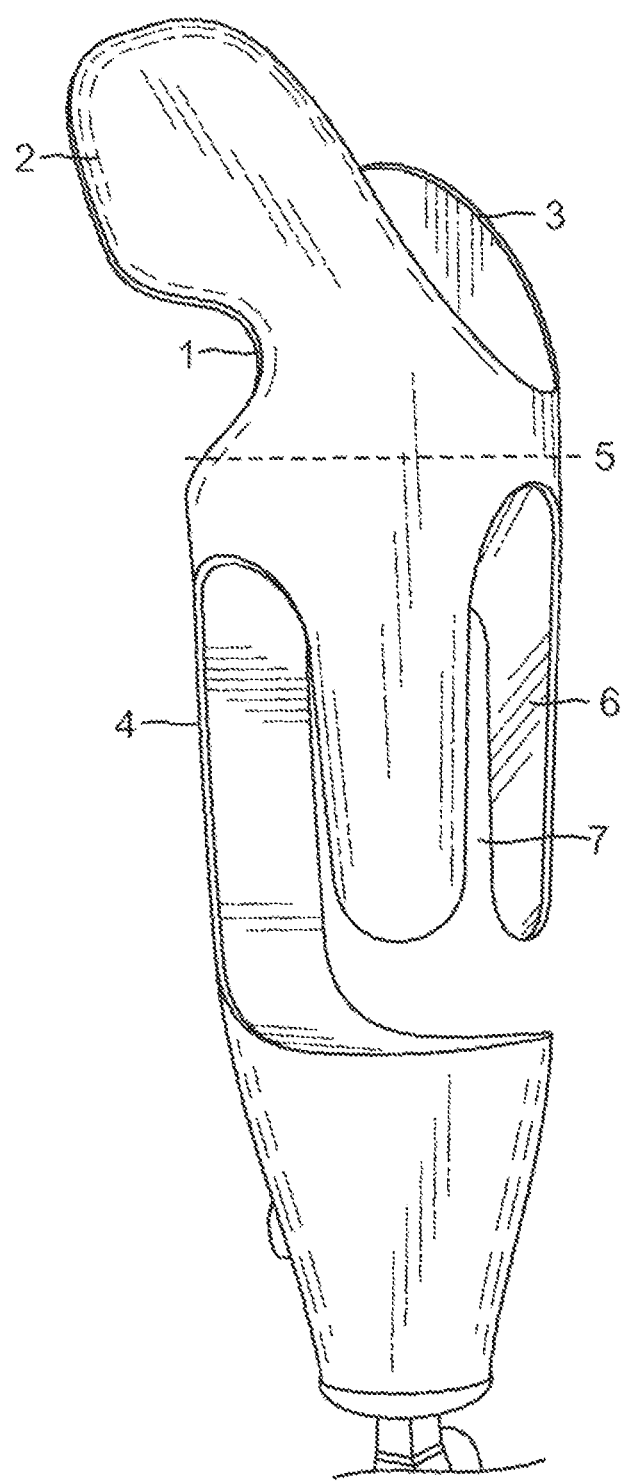
FIG. 1 is a perspective view from an anterior position of a transhumeral high-fidelity interface device in accordance with a first preferred embodiment of the invention, where the device has an open cage or strut-type structure.

As shown in FIG. 1, a the transhumeral open-cage interface embodiment, there is an upper portion 1, which has both an anterior stabilizer 2 and a posterior stabilizer 3 and which extends in a proximal (in this case toward a patient's shoulder) and medial (toward a patient's midline) direction from a lower portion 4 to stabilize the interface on a patient's body. Although stabilizers 2 and 3 are not required, they are recommended to impart or enhance rotational stability. The lower portion 4 (below line 5) has an open-cage structure. Dashed horizontal line 5 demarcates the upper and lower portions. The lower portion 4 of this open-cage embodiment has multiple, e.g. three or four struts 6, which look like fingers that extend along the long axis of the residual limb and are designed to partially encompass the residual limb, allowing soft tissue to flow through windows 7.

Figure 2:
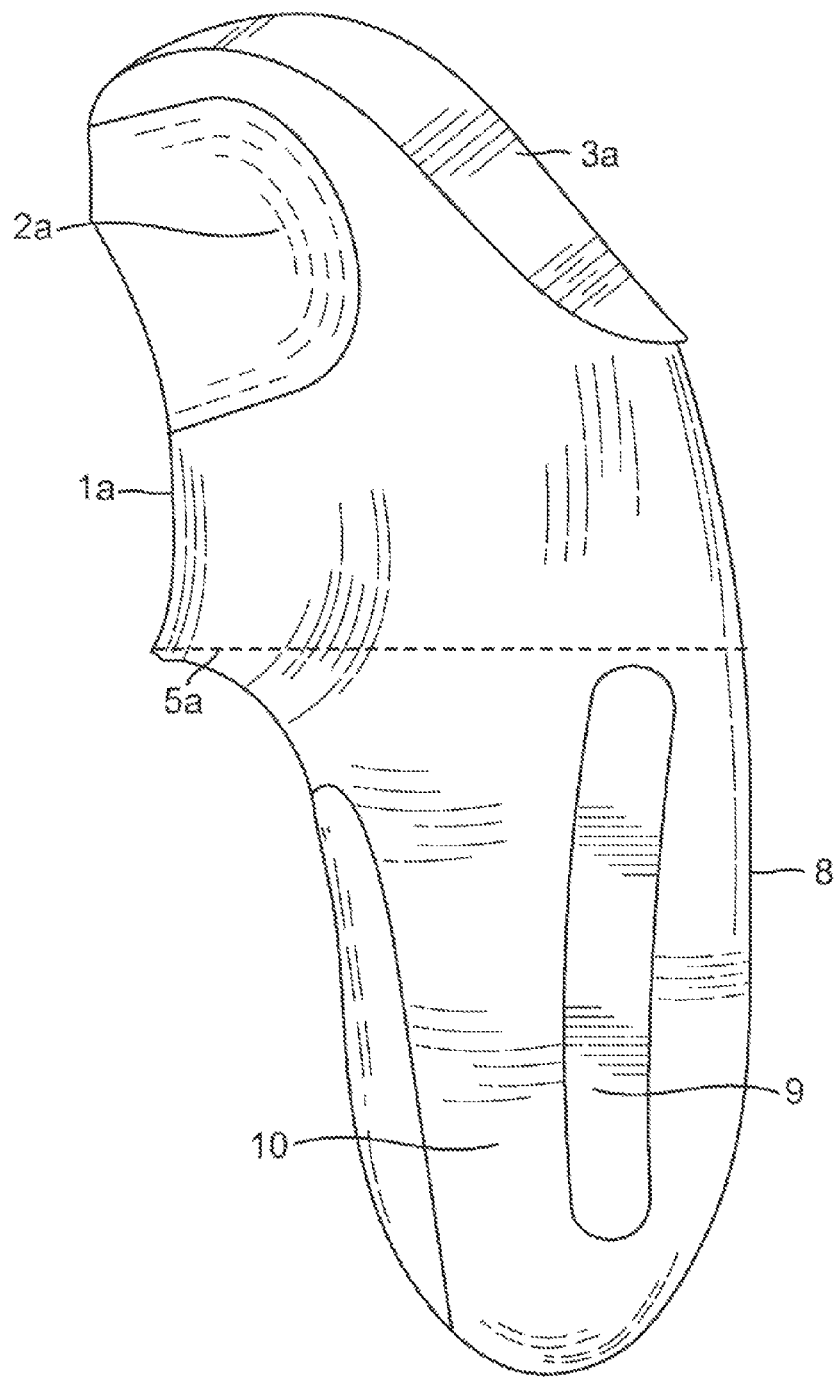
FIG. 2 is a perspective view from an anterior position of a transhumeral high-fidelity interface device in accordance with a second preferred embodiment of the invention, where the device has a closed structure.

As shown in FIG. 2, a transhumeral solid-body interface embodiment, there is an upper portion 1a, which has both an anterior stabilizer 2a and a posterior stabilizer 3a and which extends in a proximal (in this case toward the shoulder) and medial (toward the midline) direction from lower portion 8 to stabilize the interface on the body. Although stabilizers 2a and 3a are not required, they are recommended to impart or enhance rotational stability. In this embodiment, lower portion 8 is a solid body structure. A dashed horizontal line 5a demarcates the upper and lower portions. The lower portion of this solid-body embodiment has multiple, e.g. three or four, compression areas 9 and soft tissue relief areas 10 that extend along the long axis of the residual limb and are arranged circumferentially in an alternating compression-relief pattern as shown. Soft tissue relief areas 10 must have a volume sufficient to cleave displaced skin and other tissue from compression applied by compression areas 9.

Figure 3:
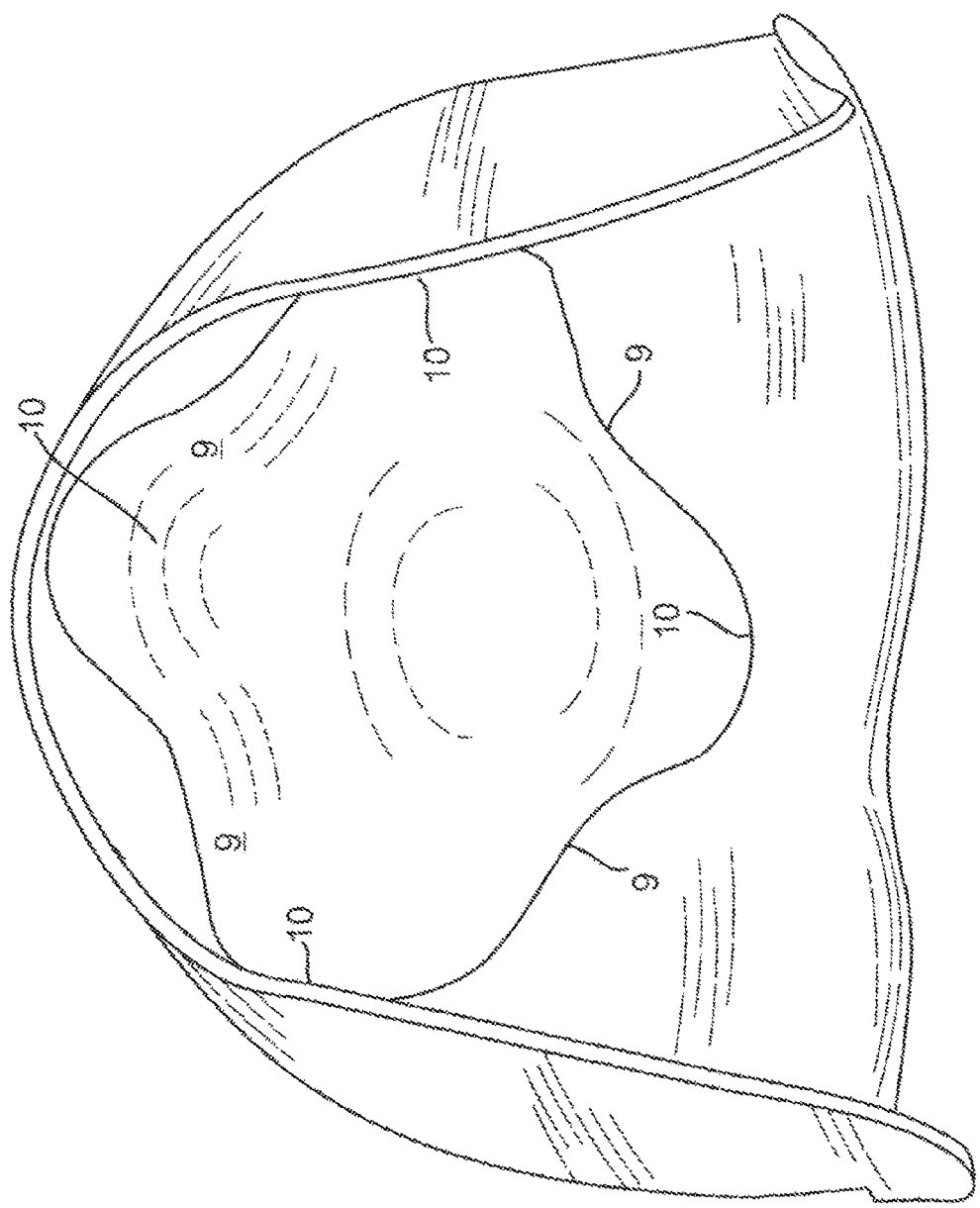
FIG. 3 is a cutaway view from the top of the interface device of FIG. 2, showing an interior thereof.

In FIG. 3, an interior of the transhumeral solid-body interface embodiment is shown, with alternating compression areas 9 and relief areas 10 indicated.

Figure 4:
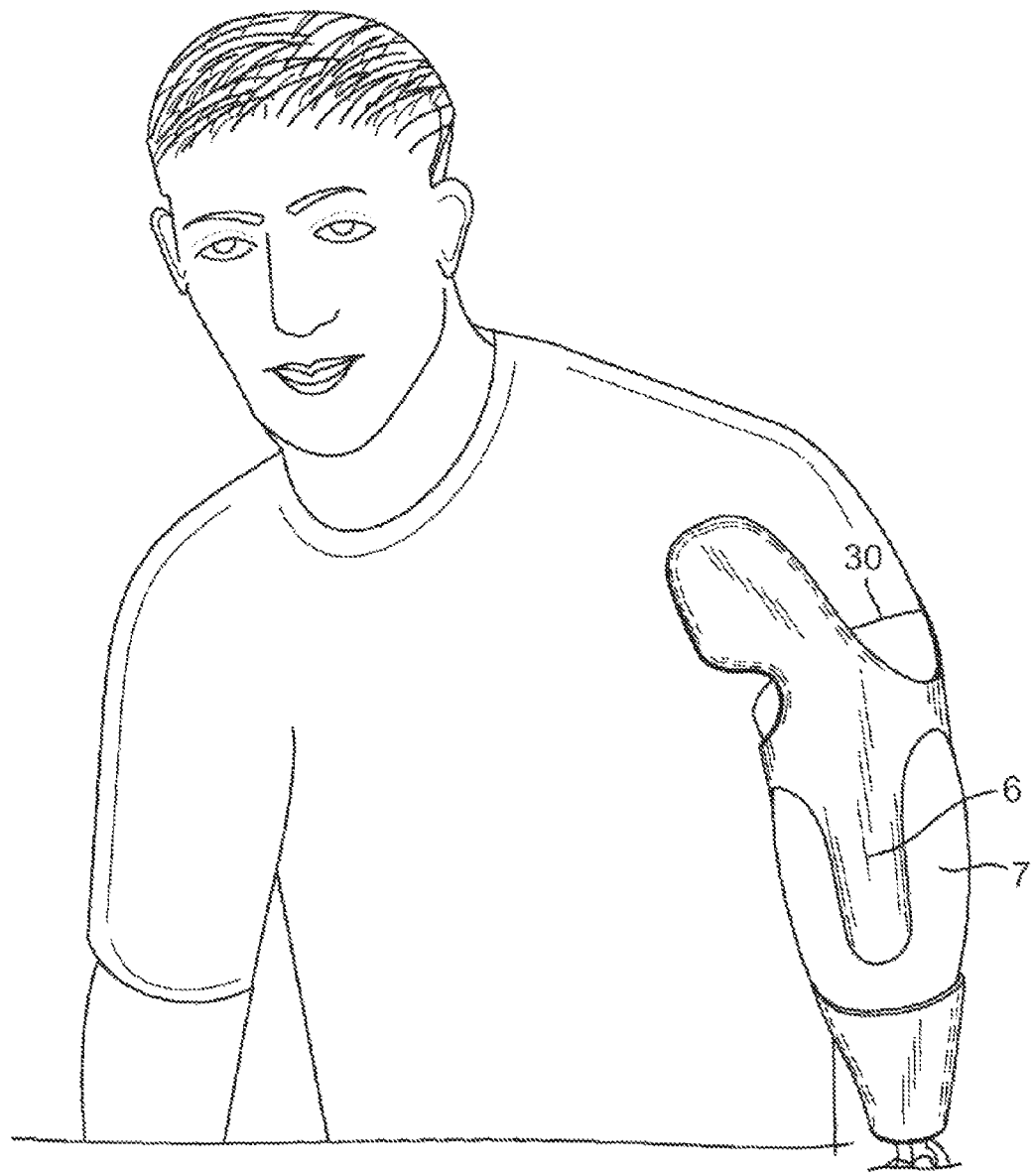
FIG. 4 is a view of the device of FIG. 1 on a patient's left arm.

In FIG. 4, a patient is shown wearing a transhumeral open-cage interface embodiment such as that of FIG. 1 with a suspension liner 30 of minimal thickness or of sufficient stretch to minimally restrict soft tissue flow through the relief windows. Struts 6 providing soft tissue compression and windows 7 allowing soft tissue flow are indicated.

Figure 5:
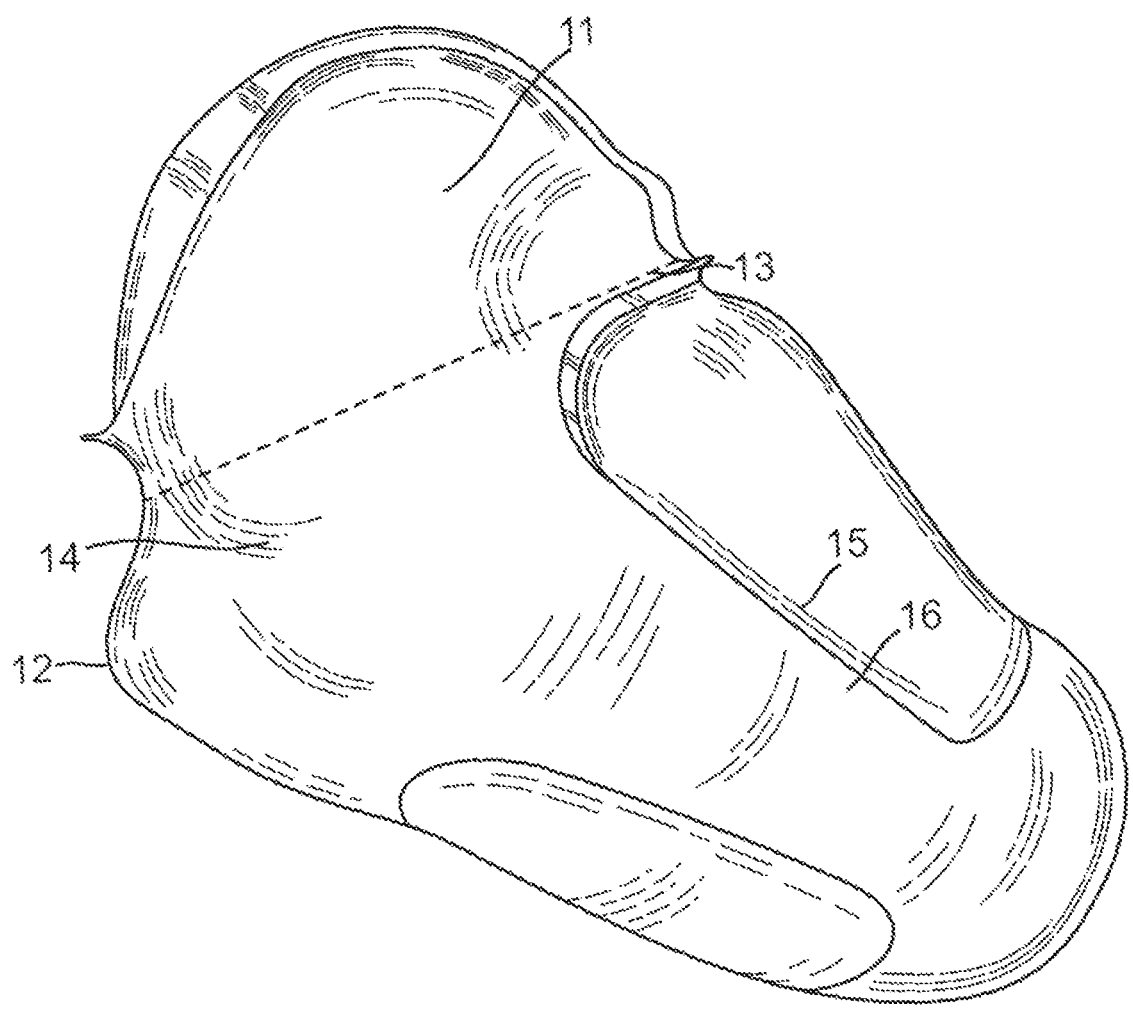
FIG. 5 is a perspective view from a medial position of a transradial high-fidelity radial interface device as a closed structure.

In FIG. 5, a transradial solid-body interface is shown. In this embodiment, there is an upper portion 11, which comprises the area of the interface proximal to olecranon 12 and cubital fold 13. A lower portion 14 has multiple, e.g. three or four, compression areas 15 and soft tissue relief areas 16 that extend along the long axis of the residual limb and are arranged circumferentially in an alternating compression-relief pattern as shown.

Figure 6:
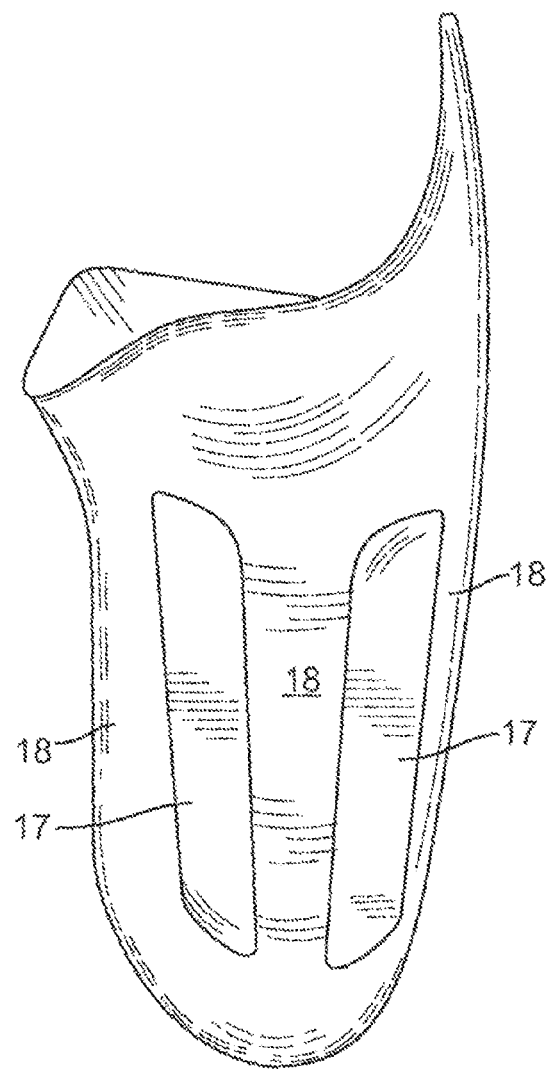
FIG. 6 is a perspective view from an anterior position of a transfemoral high-fidelity interface device in accordance with a fourth embodiment, where the device has a closed structure.

In FIG. 6, a transfemoral solid-body interface is shown. This embodiment has multiple, e.g., three or four, compression areas 17 and soft tissue relief areas 18 that extend along the long axis of the residual limb and are arranged circumferentially in an alternating compression-relief pattern as shown.

Figure 7A:
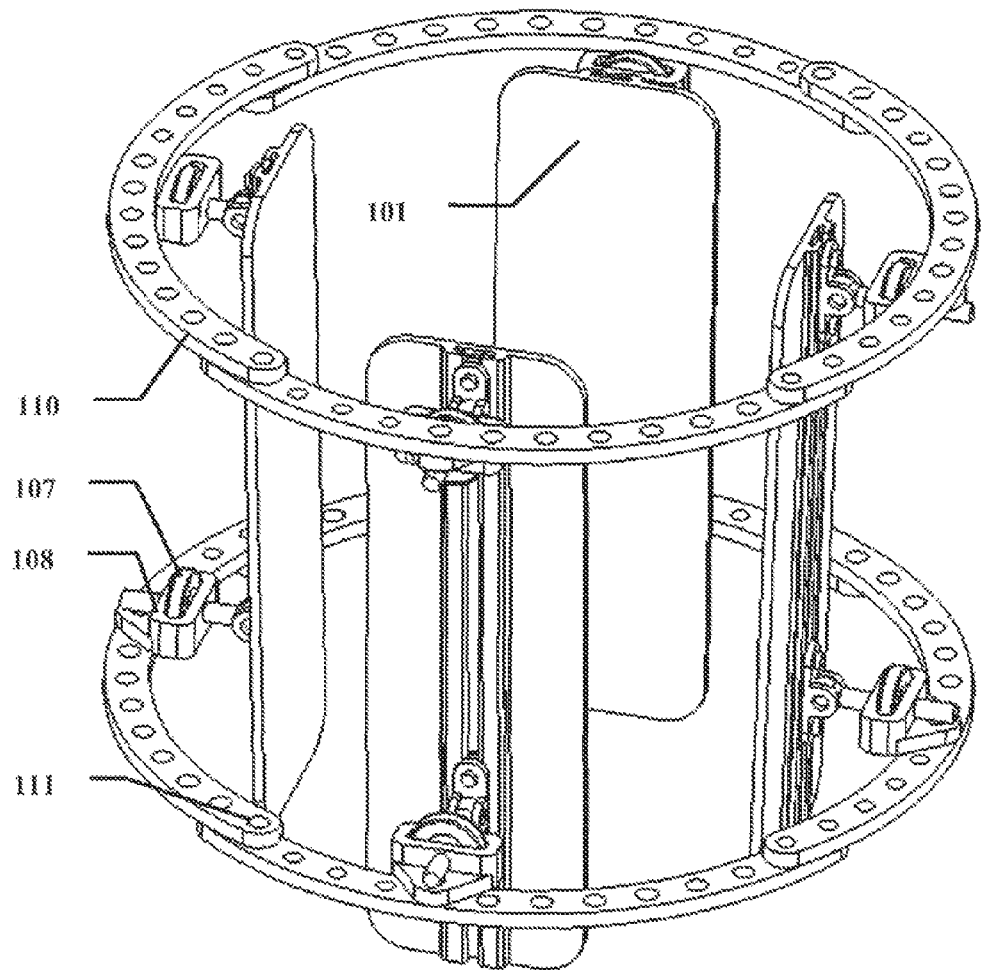
FIGS. 7a and 7b show an example of a jig design utilized for transfemoral cast taking in preparation for the creation of a transfemoral high-fidelity interface.
Figure 7B:
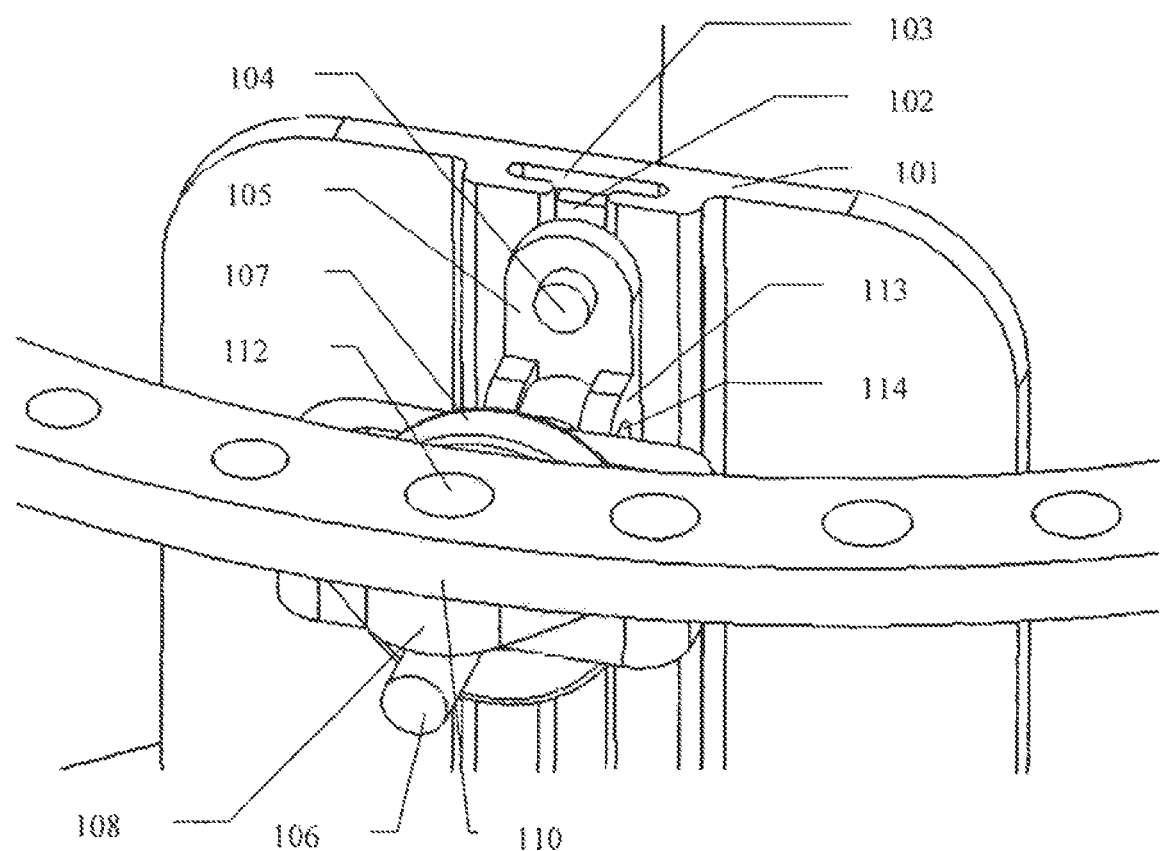

In FIGS. 7a and 7b, there is shown a tool for use in imaging (and particularly helpful for the lower limb), which tool optionally may be used with various embodiments of the invention. Imaging is a process to render a model of the limb using plaster bandage, laser scanning or other such technique. Imaging of a limb under compression may be done to create the model. This tool is essentially a connected set of adjustable bars attached to screws which in turn are connected to a circumferential or partially circumferential ring that allows this tool to be placed over the limb either before, during or after the imaging process and that applies the appropriate compression to the soft tissues of the limb in desired target areas while allowing redundant soft tissue to flow through the areas between the struts unhindered.

More specifically, the jig consists of a multiplicity of paddles 101 for pushing inward against the limb remnant of an amputee. For most purposes, four paddles preferably are used. For the configuration shown, eight sectors 110 are assembled into two rings. Eight screws are used at locations 111 to assemble the rings.

In FIG. 7b, a screw (not shown) is inserted into clearance hole 112 to secure the turnbuckle holder 108 (also shown in FIG. 7a) to the sector 110. Until the screw is tight, the holder is free to rotate with respect to the sector. The turnbuckle rod 106 is threaded with an eyelet 113 on the far end to connect to paddle holder 105. A pin attaching these two parts is inserted into hole 114. Paddles 101 each have a channel 103 into which a slider 102 is captured. This slider has two threaded bosses 104 which are secured to paddle holder 105 by nuts (not shown). By loosening these two nuts, the slider may be repositioned along the paddle.

To adjust the position of the paddle, a threaded wheel 107, shown in FIGS. 7a and 7b, is turned. In the configuration shown in FIG. 7a, there are a total of eight turnbuckle assemblies to position the paddles in contact with the amputee's limb. Preferably, the paddles are made from a rigid, inexpensive plastic that can be trimmed to a width and length suitable to the individual amputee fitting. All of the other components are preferably reusable.

Figure 8A:
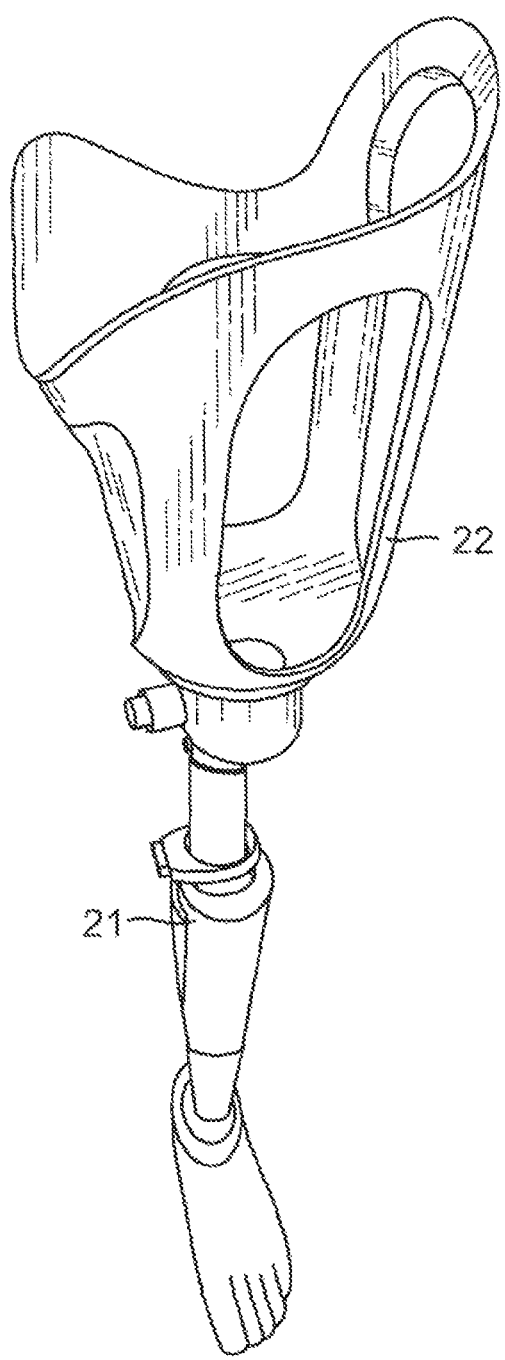
FIGS. 8a and 8b show the anterior and posterior perspectives of an exemplary transfemoral high-fidelity interface attached to prosthetic components.
Figure 8B:
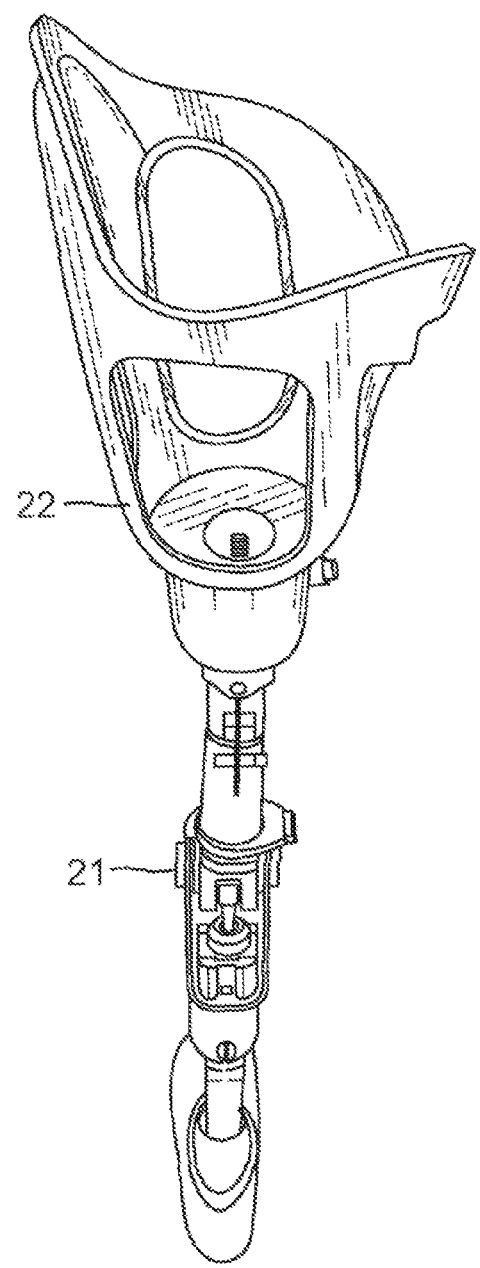

As shown in FIGS. 8a (an anterior perspective) and 8b (a posterior perspective), an exemplary prosthetic component set 21 is attached to one device 22. Various prosthetic components may be attached to the device by any one of various methods currently available or available in the future. The device may have at a proximal end any one of various support structures known in the art or developed in the future.

In a method in accordance with an embodiment of the invention, an interface device with open-cage or strut-type is fitted onto a person.

First, it is determined whether a patient needs a transradial (radial level) device, a transhumeral (humeral level) device, a transtibial (tibial level) device, or a transfemoral (femoral level) device. The patient or prosthetist may select a closed device or an open cage strut-type high-fidelity device.

Second, the patient's limb radius is determined at one or more locations. Third, the device is essentially crimped during modification or creation of the device until sufficient compression from the at rest radius of the patient's limb at the cage or strut region of the device is at a desired amount. The desired amount of compression will depend in part on the patient's bone size, body fat, and other tissue parameters at the area of the cage or strut. The compression generally is at least 20% or at least 30% from the at rest radius of the limb. Typically, compression will be from 20% to 70% or 30% to 70%. As described below for an alternative embodiment and illustrated in FIG. 15A-C, the amount of compression is sufficient such that there is minimum redundant tissue between the maximum point of compression 303 and the target bone 305 contained within the interface such that motion capture of the bone is maximized while retaining sufficient comfort to allow the wearer to withstand the compression for a useable amount of time and to ensure adequate blood flow over time, which can be ascertained through the use of a blood perfusion sensor and monitor. The blood perfusion sensor can be utilized during casting, diagnostic interface assessment or in the definitive socket.

A usable amount of time for an interface is the amount of time the operator expects the person being fitted with the interface would wear the interface on a typical day. It is to be appreciated that this amount of time is different and unrelated to the amount of time necessary to perform the imaging process described for the various embodiments of the present invention.

However, compression can be lower than 20% or higher than 70% depending upon bone size, body fat and other tissue parameters, and the prosthetist and/or physician will use the blood perfusion sensor and monitor and make a determination of the safety and effectiveness of the particular amount of compression for the particular patient.

Fourth, the modified or rectified high-fidelity device with an inner radius or inner radii of size that can be fit over the distal (free) end of the patient's limb (for fitting with a prosthesis) is selected, and applied to the patient's limb, e.g., by sliding onto the limb.

Creation and Fabrication of High-Fidelity Interface

In a method in accordance with an embodiment of the invention, an interface device with open-cage (strut-type) or solid-body configuration is fitted onto a person.

First, it is determined whether a patient needs a wrist disarticulation device, a transradial device, a transhumeral device, a symes device, a transtibial device, a knee disarticulation device, a transfemoral device or a hip disarticulation device. The patient or prosthetist may select a closed or open cage strut-type high-fidelity device as disclosed herein.

Second, the patient's limb radius is determined at one or more locations along the limb where the interface device will be fit.

Third, the interface is created using one of several different methods, all of which require modification by the prosthetist to complete fitting of such a final socket.

Figure 18:
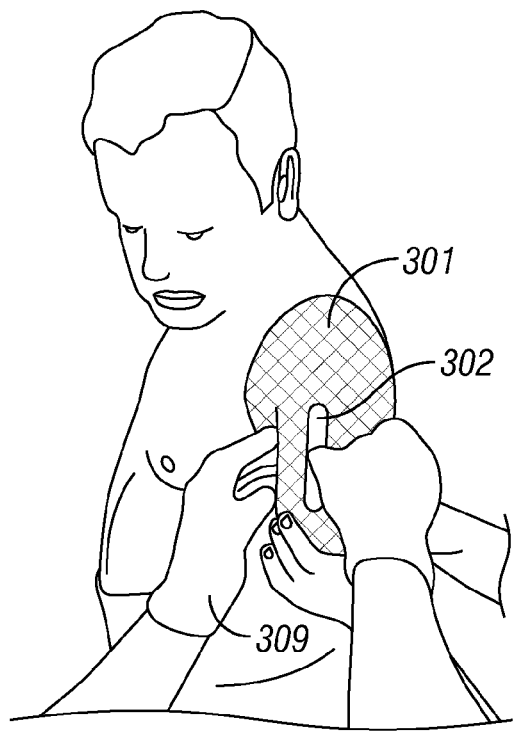
FIG. 18 is a drawing showing a technician pressing compression bars on target areas after casting material has been applied to a limb.

In FIG. 18, one method commonly employed is to cast the patient's limb utilizing a plaster bandage 301. This casting allows the prosthetist or clinician to add compression forces to the plaster wrap and hence to the limb in the target areas that will hold this compression and allow for subsequent tissue relief between these compression areas as the plaster sets.

FIG. 15A-C depicts compression bars 302 pressing against a target area of a limb and displacing tissue into relief areas 308. The amount of compression is sufficient such that there is minimum redundant tissue between the maximum point of compression 303 and the target bone 305 contained within the limb such that motion capture of the bone is maximized while retaining sufficient comfort to allow the wearer to withstand the compression for a useable amount of time and to ensure adequate blood flow over time.

FIG. 16 illustrates motion capture where compression bars 302 lie along the length of the bone 305 and press inwardly from the at rest radius of the limb 306. Absent compression bars, the bone and the maximum point of compression 303 would move outwardly to a socket wall not shown) to an area on the limb 307 approximately at the at rest radius. This represents the lost motion of the skeletal structure with respect to a prosthetic interface when force is applied between the two as would occur as an amputee tries to move the prosthesis as a whole. In a traditional socket, this lost motion occurs when the bone moves toward the socket wall a substantial distance before imparting force to the socket wall. By pressing the compression bars inwardly during casting to the maximum point of compression, lost motion within the resultant interface is minimized without causing discomfort to the user.

In FIG. 18, the cast 301, which will function as a negative model or mold, is removed and filled with liquid plaster.

The liquid plaster is allowed to set in the mold.

Once the liquid plaster has solidified, the plaster bandage 301 (mold), depicted in FIG. 18, surrounding the solid (positive) model is removed. The positive model is now revealed to which the prosthetist or clinician applies additional compression to the target areas by carving directly on the model. Carving on the positive model creates a pressure or compression point on the target areas because the "negative" model (the socket being molded from the positive model) will now have a larger inwardly facing compression area.

Another way to generate the limb shape to be modified is to use a scanner to obtain the image shape and then modify the digital image accordingly using well known software, e.g., on a computer such as a laptop. This digital model (as modified to apply targeted compression and relief) can then be sent to a carver or 3d printer to generate a physical positive model over which a negative model (mold) can be created for fitting or additional fabrication.

In order to determine appropriate compression levels, the device is essentially crimped during modification or creation of the device until sufficient compression from the at rest radius of the patient's limb at the cage or strut region of the device is at a desired amount. The desired amount of compression will depend in part on the patient's bone size, body fat, and other tissue parameters at the area of the cage or strut. The compression generally is at least 20% from the at rest radius of the limb. Typically, compression will be from 20% to 70%, or at least 30% to 70%. For certain patients, such as very muscular, or those having calcification, the minimum compression to achieve the advantages of the inventive method may be a little below the above minimum ranges, and for certain patients, such as obese patients or others with extremely fleshy skin, higher than 70% compressions may be appropriate. However, comfort and medical safety can dictate the final appropriate amount of compression for any particular patient.

The amount of compression is sufficient such that there is minimum redundant tissue between the maximum point of compression and the target bone contained within the interface such that motion capture of the bone is maximized while retaining sufficient comfort to allow the wearer to withstand the compression for a useable amount of time.

Fourth, the decision is made whether a diagnostic interface (transparent thermoplastic socket for analysis of fit and function prior to creating the definitive model) or a definitive interface, typically consisting of a laminated framework, is to be created.

Over the now modified or crimped model, in order to create the diagnostic interface, a thermoplastic material is heated and draped or blister-formed, preferably under vacuum, to render a new negative model. Once the thermoplastic has cooled and become rigid, the plaster is then removed from within the thermoplastic interface and the interface is trimmed and smoothed and is of sufficient stiffness and transparency to allow the clinician to don it on the patient and judge the fit and pressures acting on the limb. This model can be removed from the patient's limb and trimmed or heated to change its boundaries or perimeter and shape, including the amount of compression or relief that is applied to the limb based on what is observed and comments from the wearer.

In order to create the definitive interface, an acrylic laminate (with or without stiffeners such as carbon fiber, Kevlar®, i.e., para-aramid synthetic fiber, etc.) or similar can be vacuum formed directly over the model or in the case of a frame style interface with a flexible liner and rigid frame, over an inner flexible liner that has been previously vacuum-formed over the same model.

The now compressed negative socket, whether in diagnostic or definitive form can be donned by either a push-in or pull-in method, with the latter being preferred due to the high levels of compression applied to the limb. This compression imparts friction on the skin during donning and hence makes it more difficult to get all the limb tissue down in the interface unless a donning sock or similar is used to pull the tissue in. The pull-in method utilizes a donning sock or similar such device that surrounds the limb and is pulled through a distal aperture at the distal end or bottom of the interface. As the wearer pulls down on the end of the donning sock and pulls it through the aperture, the limb is pulled down into the interface until fully seated.

Figure 9:
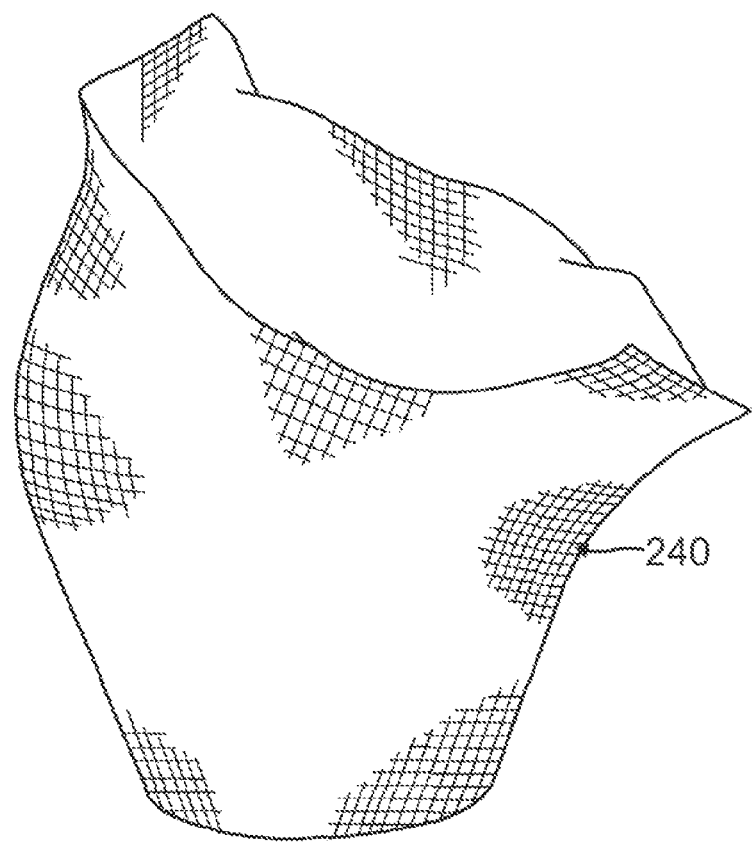
FIG. 9 is a drawing showing a casting

In FIG. 9, an example of a casting 240, e.g., for an upper limb, is shown.

Figure 10:
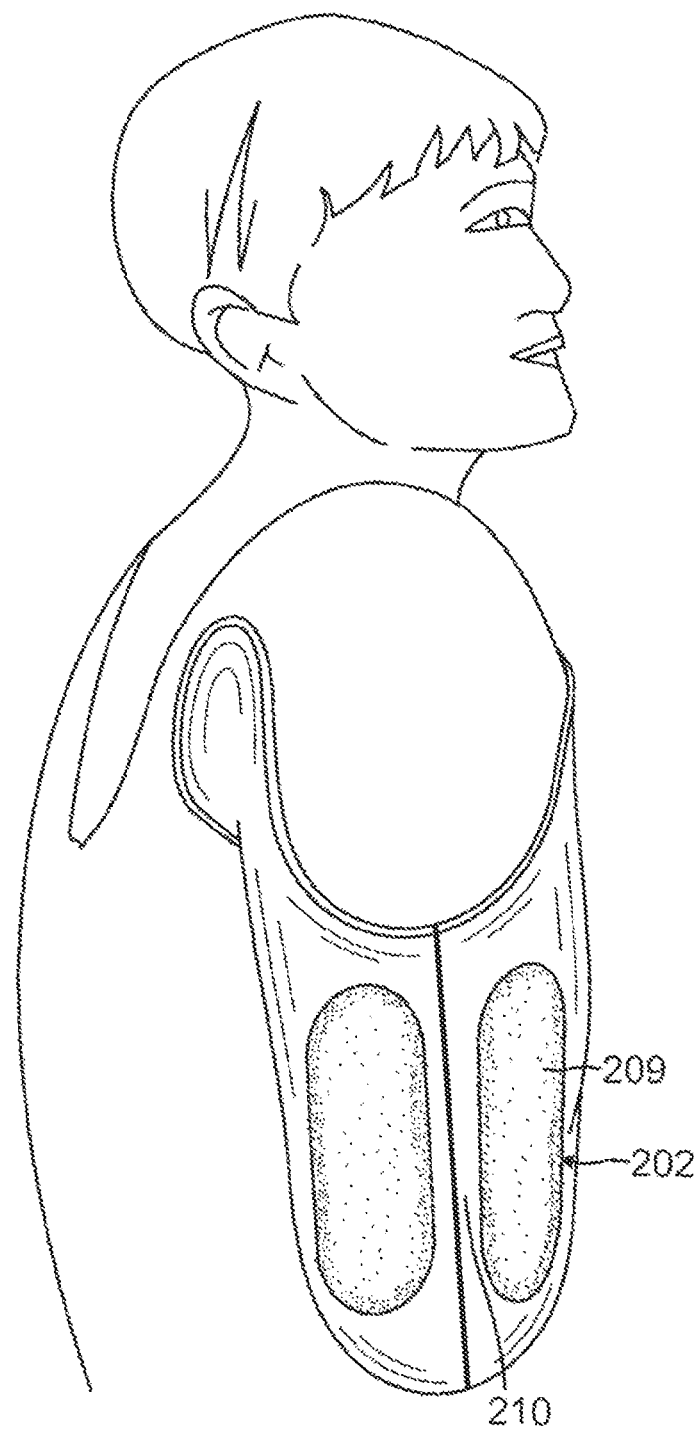
FIG. 10 is a drawing showing a mold formed from the casting.

In FIG. 10, a socket 202 having compression regions 209 and relief regions 210 is shown on a patient's limb, e.g., an upper limb.

Figure 11:
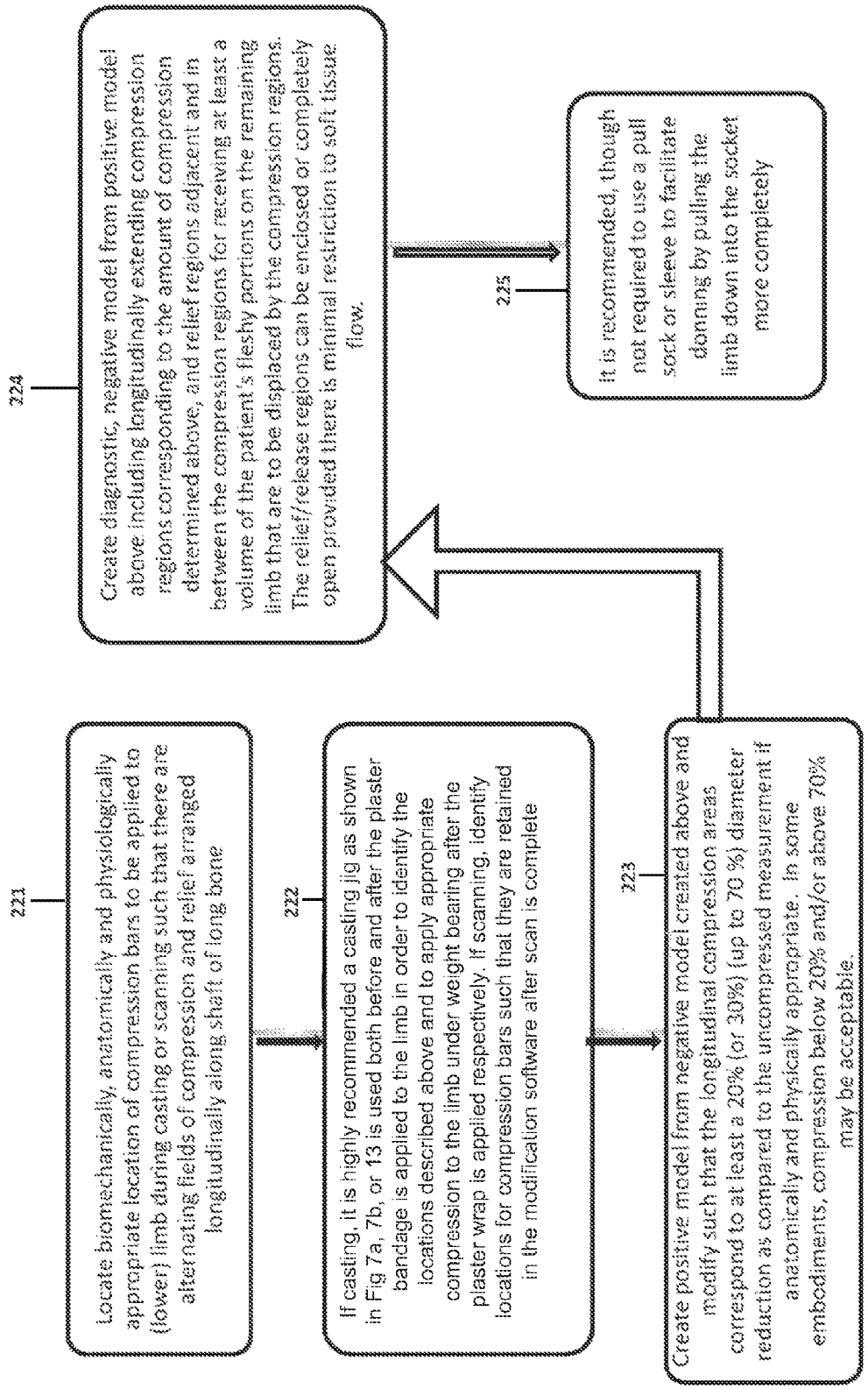
FIG. 11 is a flow chart showing steps in a process of an embodiment of the invention for making a high-fidelity interface for a prosthesis and limb, preferably a lower limb.
Figure 12:
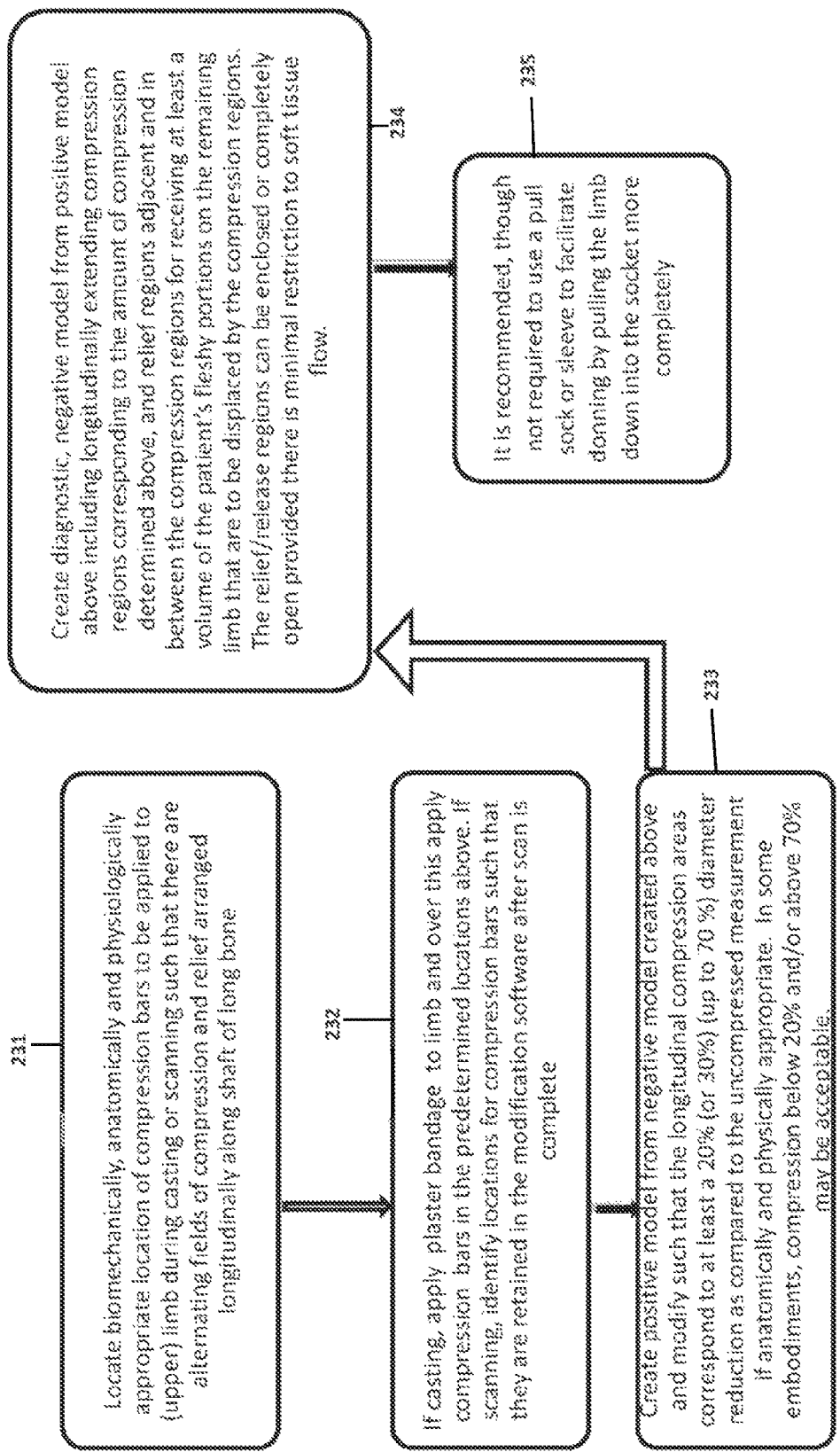
FIG. 12 is a flow chart showing steps in an alternate process of another embodiment of the invention for making a high-fidelity interface for a prosthesis and limb, preferably an upper limb.

FIG. 11 is a flow chart showing steps in a process of an embodiment of the invention for making a high-fidelity interface for a prosthesis and limb, preferably a lower limb, the lower limbs being the ones that will be bearing weight of the wearer's body; and FIG. 12 is a flow chart showing steps in an alternate process of another embodiment of the invention for making a high-fidelity interface for a prosthesis and limb, preferably an upper limb.

Figure 17:
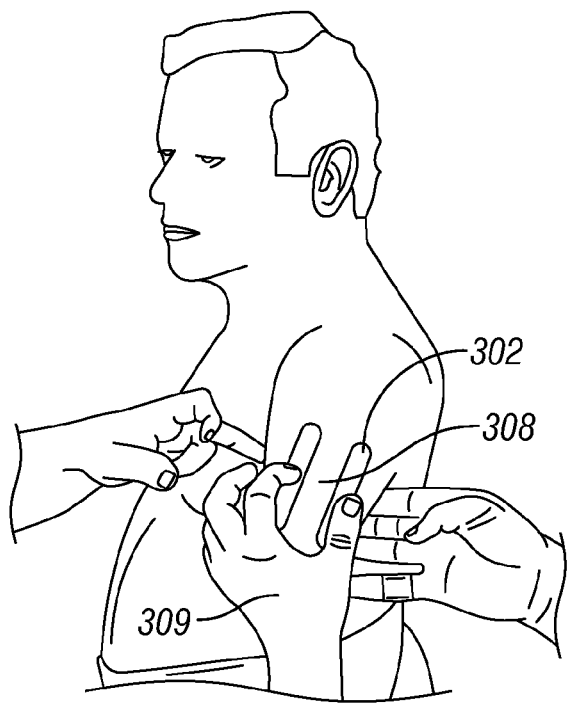
FIG. 17 is a drawing showing the hands of a technician locating compressions bars over target areas where compression is desired, while allowing displacement of tissue into noncompressed areas.

In FIG. 11, in a step 221 and as depicted in FIG. 17 (for an upper limb), a technician will locate biomechanically, anatomically and physiologically appropriate location of compression bars to be applied to a lower limb during casting or scanning such that there are alternating compression areas (under the compression bars 302) and relief areas 308 arranged longitudinally along shaft of long bone.

Figure 13:
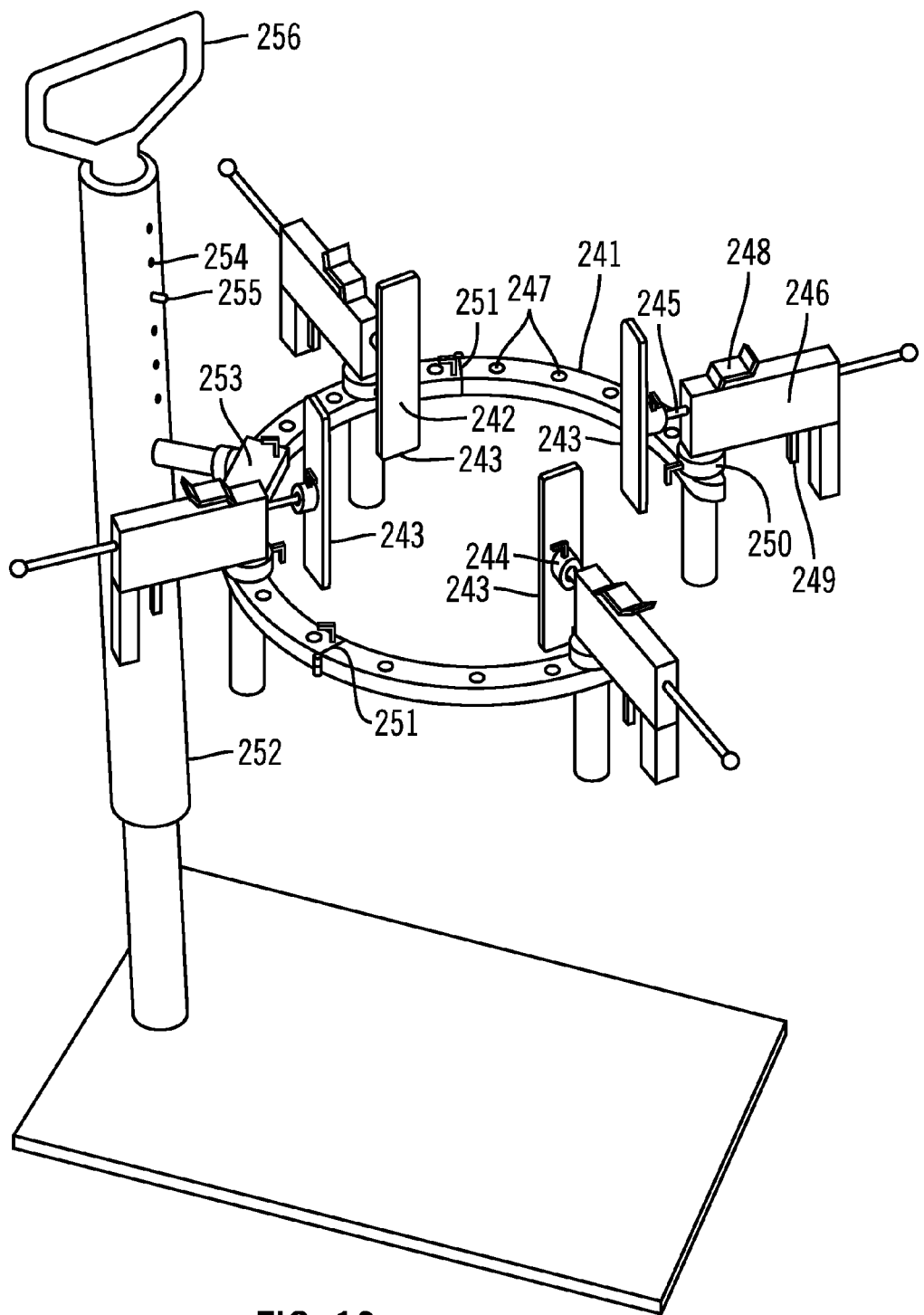
FIG. 13 is a drawing showing a jig with a single support member and stand.

In step 222, a technician will, if casting, preferably use a casting jig as shown in FIG. 7a, 7b, or FIG. 13, both before and after the plaster bandage 301 (depicted in FIG. 18) is applied to the limb, in order to identify the locations described above and to apply appropriate compression to the limb underweight bearing conditions after the plaster wrap is applied respectively. If scanning, the technician will identify locations for compression bars such that they are retained in the modification software after scan is complete.

In step 223, a technician will create positive model from negative model created above and modify such that the longitudinal compression areas correspond to at least a 20% (or 30%) (up to 70%) diameter reduction as compared to the uncompressed measurement if anatomically and physically appropriate. In some cases, compression below 20% or above 70% may be acceptable.

In step 224, a technician will create a diagnostic, negative model from the positive model above including longitudinally extending compression regions corresponding to the amount of compression determined above, and relief regions adjacent and in between the compression regions for receiving at least a volume of the patient's fleshy portions on the remaining limb that are to be displaced by the compression regions. The relief/release regions can be enclosed or completely open provided there is minimal restriction to soft tissue flow.

In step 225, which is optional, one preferably will put on al sock or sleeve to facilitate donning by pulling the limb down into the socket more completely.

In the process of FIG. 12, in step 231, and as depicted in FIG. 17, a technician will locate biomechanically, anatomically and physiologically appropriate location of compression bars to be applied to (upper) limb during casting or scanning such that there are alternating compression areas (under the compression bars 302) and relief areas 308 arranged longitudinally along shaft of long bone.

In step 232 and as depicted in FIG. 18, the technician will, if casting, apply a plaster bandage 301 to limb and over this apply compression bars 302 in the predetermined locations above. If scanning, the technician will identify locations for compression bars such that they are retained in the modification software after scan is complete.

In step 233, the technician will, create positive model from negative model created above and modify such that the longitudinal compression areas correspond to at least a 20% (or 30%) (up to 70%) diameter reduction as compared to the uncompressed measurement if anatomically and physically appropriate. In some cases, compression below 20% or above 70% may be acceptable.

In step 234, the technician will create a diagnostic, negative model from the positive model above including longitudinally extending compression regions corresponding to the amount of compression determined above, and relief regions adjacent and in between the compression regions for receiving at least a volume of the patient's fleshy portions on the remaining limb that are to be displaced by the compression regions. The relief/release regions can be enclosed or completely open provided there is minimal restriction to soft tissue flow.

In step 235, which is optional, one preferably will put on al sock or sleeve to facilitate donning by pulling the limb down into the socket more completely.

In FIG. 13, there is shown another embodiment of a tool for use in imaging. This embodiment includes a support member 241 for positioning paddle surfaces 242 against target areas. In the embodiment depicted, four paddles 243 are used. The paddles can pivot on a detachable, lockable paddle joint 244, such as a lockable ball joint, between the paddle and a projection member 245 to allow each paddle to pivot to the desired angle relative to the target area and to allow different sized and shaped paddles to be installed on the projection member.

The projection member 245 is connected to and actuated by an attachment mechanism 246 and the attachment mechanism is attachable to the support member 241. A slider 102, channel 103, threaded bosses 104, and paddle holder 105, as depicted in FIG. 7b, can also be included in the embodiment shown in FIG. 13 for added maneuverability of the paddle surfaces 242, in which case the projection member would attach to the paddle holder, not directly to the paddle 243.

The attachment mechanism 246 can be the same as the turnbuckle holder 108 depicted in FIG. 7b, or it could be an alternative structure which similarly allows movement, locking, and removal of the attachment mechanism at a plurality of positions 247 along the support member 241.

The projection member 245 and its actuating mechanism can have a structure such as the turnbuckle rod 106 and threaded wheel 107 depicted in FIG. 7b. Alternatively, as depicted in FIG. 13, the projection member 245, locking mechanism 248, selectable actuating mechanism 249, and attachment mechanism 246 can have the structure of a ratchet rod gun assembly.

For added maneuverability, the attachment mechanism 246 can be connected to the support member 241 by a detachable, lockable support bar joint 250, such as a lockable ball joint, so that the attachment mechanism can be rotated about the axes of the support member. This support bar joint can be in addition to the detachable, lockable paddle joint 244 at the paddle 243. Alternatively, the support bar joint 250 can be an optional configuration that allows the paddle 243 to be rigidly connected to the projection member 245.

The support member 241 includes lockable hinges 251, so that the portions of the support member lying distal to the stand 252 can move outwardly from the long axis of the stand to allow ingress and egress of the body part to be imaged.

The stand 252 is suitable to support a patient. The support member 241 can be attached to the stand with a detachable, lockable stand connector 253, such as a lockable ball joint, at a plurality of locations 254 to adjust to the size of the patient and the desired imaging area. Alternatively, the stand can be constructed of an inner and outer cylinder to allow it to telescope upwardly or downwardly and lock into position with a spring-loaded button 255. To further support the patient, a handle 256 can be included on the upper end of the stand.

The support member 241 can pivot on the stand connector 253, to allow the support member and the paddles 243 attached to the support member to be maneuvered into a desired position for imaging. Stand connector 253 also allows different sized and shaped support members to be attached and used with the stand.

Figure 14:
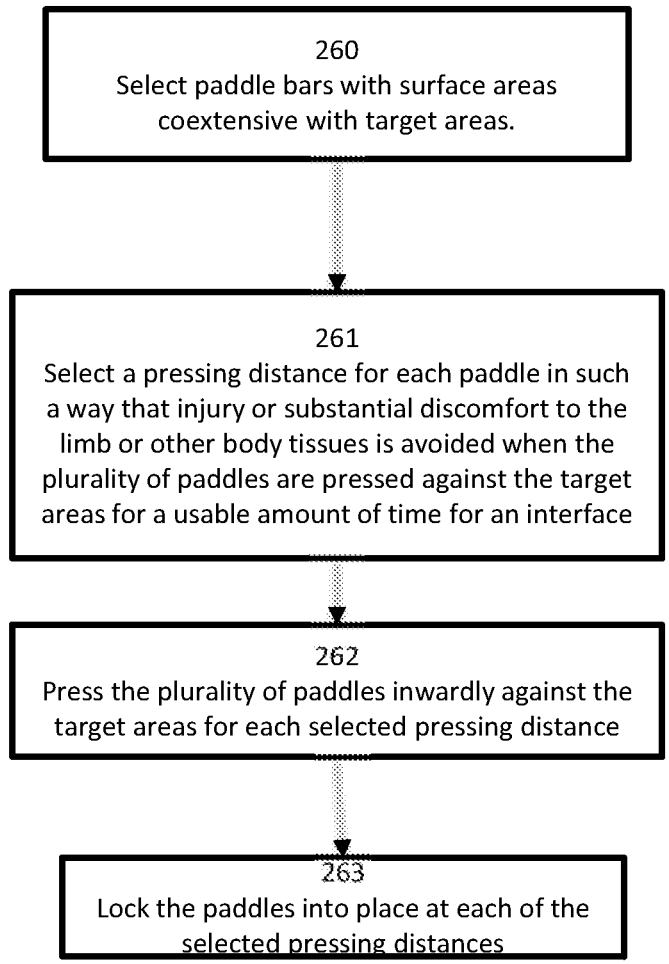
FIG. 14 is a flow chart showing steps in a process of an embodiment of the invention for imaging.
Figure 19:
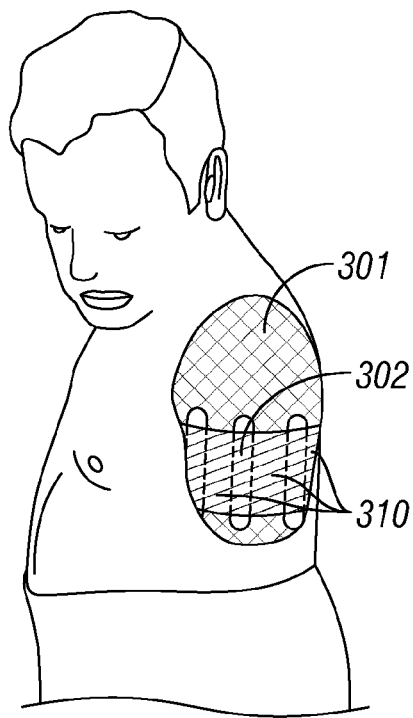
FIG. 19 is a drawing showing compression bars pressed in place using elastic wrapping material.

FIG. 14 is a flow chart showing steps in a process of an embodiment of the invention for imaging. Depending on the body part involved and the preferences of the operator, the process can be performed with the jig as shown in FIG. 7a and FIG. 7b, or with the jig shown in FIG. 13. As shown in FIGS. 17 and 18, the process can also be performed with the operator's hands 309 or, as shown in FIG. 19, by using a wrapping material 310, preferably wrapping material at least partially including material with elastic properties.

In step 260, an operator selects paddle bars with surface areas coextensive with the target areas. In step 261, the operator selects a pressing distance for each paddle in such a way that injury or substantial discomfort to the limb or other body tissues is avoided when the plurality of paddles are pressed against the target areas for a usable amount of time for an interface.

In step 262, the operator presses the plurality of paddles against the target areas by moving each of the paddles inwardly against the target area for the selected pressing distance for each paddle. Finally, in step 263, the operator locks each paddle into place at the selected pressing distance for each paddle.

Although the invention has been described using specific terms, devices, and/or methods, such description is for illustrative purposes of the preferred embodiment(s) only. Changes may be made to the preferred embodiment(s) by those of ordinary skill in the art without departing from the scope of the present invention, which is set forth in the following claims. In addition, it should be understood that aspects of the preferred embodiment(s) generally may be interchanged in whole or in part.

What is claimed is:

1. A system for imaging a body part having a skeletal structure lying within the body part, and a plurality of areas of compression on the external surface of the system comprising:
   a first projectable member operable to press a first paddle inwardly against the body part to a first pressing distance selectable for the first paddle; and
   a second projectable member coupled to the first projectable member and operable to press a second paddle inwardly against the body part to a second pressing distance selectable for the second paddle,
   wherein the first paddle and second paddle are externally disposable in opposition to each other around the longest length of the body part,
   wherein each paddle is adapted to extend substantially the longest length of the skeletal structure lying within the body part,
   wherein a narrowest width of each paddle is adapted to be at least approximately 15% of the body part width,
   wherein broadest width of each paddle is adapted to permit a plurality of noncompressed areas between each paddle for displacement of tissue of the body part when the first paddle is operated to the first pressing distance and the second paddle is operated to the second pressing distance,
   wherein the first pressing distance and the second pressing distance are selected in such a way as to be adapted to prevent substantial movement of the skeletal structure within the body part.

2. The system of claim 1, wherein the first projectable member and the second projectable member comprises a jig, wherein the jig includes:
   a first paddle attachment mechanism;
   a second paddle attachment mechanism; and
   a support member,
   wherein the first paddle attachment mechanism is connectable to the support member and to the first projectable member,
   wherein the second paddle attachment mechanism is connectable to the support member and to the second projectable member.

3. The system of claim 2, wherein the system is adapted to be used for a body part belonging to a human or animal and the system further comprises:
   a stand; and
   a stand connector,
   wherein the stand is deployable to support the human or animal,
   wherein the stand connector adjustably attaches the support member to the stand in such a way that the paddles attached to the support member are maneuverable around the longest length of the body part.

4. The system of claim 3, wherein the system is adapted to be used for a human or animal having a predetermined weight range,
   wherein the stand is structurally sufficient to at least partially support the human or animal at the predetermined weight range.

5. The system of claim 2, wherein the first paddle attachment mechanism includes a locking mechanism for the first projectable member,
   wherein the locking mechanism is operable to lock the first projectable member in place.

6. The system of claim 2, wherein the first paddle attachment mechanism is connectable to the support member at a plurality of positions on the support member.

7. The system of claim 1, wherein an imaging material lies between the first paddle and the body part and the second paddle and the body part.

8. The system of claim 7, wherein the imaging material is a casting material.

9. The system of claim 1, wherein the system is adapted to be used for imaging a limb.

10. The system of claim 1, wherein the system is adapted to be used for a body part belonging to a human or animal of a predetermined weight range,
    wherein the system further comprises a stand structurally sufficient to at least partially support the human or animal of the predetermined weight range.

11. The system of claim 1, wherein the inwardly facing surface of the first paddle is substantially flat.

12. A system for imaging a limb of a human or animal having a skeletal structure lying within the limb, and a plurality of areas of compression on the external surface of the limb along a longest length of the skeletal structure wherein the plurality of areas of compression are selected in such a way as to prevent substantial movement of the skeletal structure within the limb, the system comprising a jig, the jig including:
    a support member;
    a plurality of bars, including:
    a first paddle; and
    a second paddle,
    wherein the first paddle includes a first bar surface area that is substantially coextensive to a first target area chosen from the plurality of areas of compression,
    wherein the second paddle includes a second bar surface area that is substantially coextensive to a second target area chosen from the plurality of areas of compression,
    wherein each target area is adapted to extend substantially the longest length of the skeletal structure lying within the limb,
    wherein a narrowest width of each target area is adapted to be at least approximately 15% of the limb width
    wherein a broadest width of each target area is adapted to permit a plurality of noncompressed areas between each target area for displacement of tissue of the limb;
    a first bar attachment mechanism;
    a second bar attachment mechanism,
    wherein the first bar attachment mechanism is connectable to the support member at one of a plurality of positions on the support member,
    wherein the second bar attachment mechanism is connectable to the support member at another of the plurality of positions on the support member;
    a pressing tool, including:
    a first projectable member operable by the first bar attachment mechanism to press the first paddle inwardly against the limb at the first target area to a first pressing distance for the first paddle, wherein the first bar attachment mechanism is operable to lock the first projectable member in place at the first pressing distance; and
    a second projectable member operable to press the second paddle inwardly against the limb at the second target area to a second pressing distance for the second paddle,
    wherein the second bar attachment mechanism is operable to lock the second projectable member in place at the second pressing distance,
    wherein the first pressing distance and the second pressing distance are adapted to be selected in such a way that injury or substantial discomfort to the limb or other body tissues is avoided when the first projectable member and the second projectable member are applied for a usable amount of time for an interface,
    wherein the pressing tool is adapted to prevent substantial movement of the skeletal structure within the limb,
    wherein the pressing tool is adapted to further permit displacement of tissue of the limb from the plurality of areas of compression into the plurality of noncompressed areas.

13. The system of claim 12, further comprising
    a stand; and
    a stand connector,
    wherein the stand is deployable to support the human or animal,
    wherein the stand connector adjustably attaches the support member to the stand in such a way that the plurality of bars attached to the support member are maneuverable to press against the limb at the plurality of areas of compression.

14. A tool for imaging a body part having a skeletal structure lying within the body part, and a plurality of areas of compression on the external surface of the body part wherein the plurality of areas of compression are selected in such a way as to prevent substantial movement of the skeletal structure within the body part, the tool comprising:
    a plurality of bars, including:
    a first paddle; and
    a second paddle,
    wherein the first paddle includes a first bar surface area that is substantially coextensive to a first target area chosen from the plurality of areas of compression,
    wherein the second paddle includes a second bar surface area that is substantially coextensive to a second target area chosen from the plurality of areas of compression
    wherein each target area is adapted to extend substantially the longest length of the skeletal structure lying within the body part,
    wherein a narrowest width of each target area is adapted to be at least approximately 15% of the body part width
    wherein a broadest width of each target area is adapted to permit a plurality of noncompressed areas between each target area for displacement of tissue of the body part.

15. A method for imaging a body part having a skeletal structure lying within the body part, and a plurality of areas of compression on the external surface of the body part wherein the plurality of areas of compression are selected in such a way as to prevent substantial movement of the skeletal structure within the body part, the method comprising:
    selecting a plurality of bars,
    wherein the step of selecting a plurality of bars comprises:
    selecting a first paddle; and
    selecting a second paddle,
    wherein the first paddle includes a first bar surface area that is substantially coextensive to a first target area chosen from the plurality of areas of compression, wherein the second paddle includes a second bar surface area that is substantially coextensive to a second target area chosen from the plurality of areas of compression; and pressing the plurality of bars, wherein the step of pressing the plurality of bars comprises:

pressing the first paddle inwardly against the body part at the first target area to a first pressing distance selectable for the first paddle; and pressing the second paddle inwardly against the body part at the second target area to a second pressing distance selectable for the second paddle, wherein the step of pressing the plurality of bars prevents substantial movement of the skeletal structure within the body part, wherein the step of pressing the plurality of bars further permits displacement of tissue of the body part from the plurality of areas of compression into a plurality of noncompressed areas wherein the first pressing distance and the second pressing distance are selected in such a way that injury or substantial discomfort to the body part or other body tissues would be avoided were the step of pressing the first paddle and the step of pressing the second paddle applied for a usable amount of time for wearing an interface creating an image of the body part.

16. The method of claim 15, wherein the step of pressing the plurality of bars is performed using a jig, the jig including:

a bar attachment mechanism; and a support member, wherein the bar attachment mechanism is connectable to the support member and to at least one of the plurality of bars.

17. The method of claim 16, wherein the bar attachment mechanism includes a projectable member, the method further comprising: operating the projectable member to project at least one of the first paddle for the first pressing distance and the second paddle for the second pressing distance.

18. The method of claim 17, wherein the bar attachment mechanism includes a locking mechanism for the projectable member, wherein the step of operating the projectable member further comprises: locking the projectable member in place using the locking mechanism.

19. The method of claim 16, wherein the body part belongs to a human or animal and the method further comprises:

attaching the support member to a stand using a stand connector, wherein the stand is deployable to support the human or animal; and maneuvering the support member using the stand connector in such a way that the plurality of bars attached to the support member are placed in position to press against the body part at the plurality of areas of compression.

20. The method of claim 19, wherein the human or animal has a predetermined weight range, wherein the stand is structurally sufficient to at least partially support the human or animal at the predetermined weight range.

21. The method of claim 16, further comprising: connecting the bar attachment mechanism to the support member at one of a plurality of positions on the support member.

22. The method of claim 15, wherein the narrowest width of each target area is at least approximately 15% of the body part width and the broadest width of each target area permits the plurality of noncompressed areas between each target area for displacement of tissue of the body part.

23. The method of claim 22, wherein each target area extends substantially the longest length of the skeletal structure lying within the body part.

24. The method of claim 15, wherein the step of pressing the plurality of bars includes pressing and holding the plurality of bars in place using a wrapping material.

25. The method of claim 24, wherein the wrapping material includes an elastic material.

26. The method of claim 15, wherein an imaging material lies between the first paddle and the body part and the second paddle and the body part.

27. The method of claim 26, wherein the imaging material is a casting material.

28. The method of claim 15, wherein the body part is a limb.

29. The method of claim 15, wherein the interface is a socket.

30. The method of claim 15, wherein the step of pressing the plurality of bars includes pressing and holding the plurality of bars in place by hand.

31. The method of claim 15, further comprising: selecting the first bar surface area and second bar surface area in such a way that the plurality of noncompressed areas is equal to or greater in number than the plurality of areas of compression.

32. The method of claim 15, wherein the body part belongs to a human or animal of a predetermined weight range, the method further comprising: supporting the human or animal using a stand designed to at least partially support the predetermined weight range.

33. The method of claim 15, wherein the first bar surface is substantially flat.

34. A method for imaging a limb of a human or animal having a skeletal structure lying within the limb, and a plurality of areas of compression on the external surface of the limb along a longest length of the skeletal structure wherein the plurality of areas of compression are selected in such a way as to prevent substantial movement of the skeletal structure within the limb, the method comprising:

selecting a plurality of bars, wherein the step of selecting a plurality of bars comprises:

selecting a first paddle; and selecting a second paddle, wherein the first paddle includes a first bar surface area that is substantially coextensive to a first target area chosen from the plurality of areas of compression, wherein the second paddle includes a second bar surface area that is substantially coextensive to a second target area chosen from the plurality of areas of compression, wherein each target area extends substantially the longest length of the skeletal structure lying within the limb, wherein the narrowest width of each target area is at least approximately 15% of the limb width wherein the broadest width of each target area permits a plurality of noncompressed areas between each target area for displacement of tissue of the limb, wherein a first bar attachment mechanism is connected to a support member at one of a plurality of positions on the support member, wherein the first bar attachment mechanism connects a first projectable member operable to press inwardly against the first paddle, wherein a second bar attachment mechanism is connected to the support member at another of the plurality of positions on the support member, wherein the second bar attachment mechanism connects a second projectable member operable to press inwardly against the second paddle;

selecting a first pressing distance and a second pressing distance in such a way that injury or substantial discomfort to the limb or other body tissues would be avoided were the first projectable member and the second projectable member pressed against the limb for a usable amount of time for wearing an interface;

pressing the plurality of bars, wherein the step of pressing the plurality of bars comprises:

operating the first bar attachment mechanism to move the first projectable member inwardly against the first paddle to press the first paddle surface area against the limb at the first target area to the first pressing distance;

operating the first bar attachment mechanism to lock the first projectable member in place at the first pressing distance;

operating the second bar attachment mechanism to move the second projectable member inwardly against the second paddle to press the second paddle surface area against the limb at the second target area to the second pressing distance; and operating the second bar attachment mechanism to lock the second projectable member in place at the second pressing distance, wherein the step of pressing the plurality of bars prevents substantial movement of the skeletal structure within the limb, and wherein the step of pressing the plurality of bars further permits displacement of tissue of the limb from the plurality of areas of compression into the plurality of noncompressed areas.

35. The method of claim 34, further comprising: deploying and maneuvering a stand and a stand connector in such a way that the plurality of bars attached to the support member are positioned for the operation of pressing the plurality of bars, wherein the stand is connected to the support member using the stand connector.

* * * * *

UNITED STATES PATENT AND TRADEMARK OFFICE
CERTIFICATE OF CORRECTION

| | | |
|---|---|---|
| PATENT NO. | : 8,656,918 B1 | Page 1 of 1 |
| APPLICATION NO. | : 13/334952 | |
| DATED | : February 25, 2014 | |
| INVENTOR(S) | : Randall D. Alley and T. Walley Williams, III | |

It is certified that error appears in the above-identified patent and that said Letters Patent is hereby corrected as shown below:

In the Claims

Column 16, Lines 17-18, Claim 1 delete "body part, and a plurality of areas of compression on the external surface of the system" and insert -- body part, the system --, therefor.

Column 16, Line 35, Claim 1 delete "wherein broadest" and insert -- wherein a broadest --, therefor.

Signed and Sealed this
Ninth Day of September, 2014

Michelle K. Lee
*Deputy Director of the United States Patent and Trademark Office*